(12) United States Patent
Yamada et al.

(10) Patent No.: US 9,033,866 B2
(45) Date of Patent: May 19, 2015

(54) ADVANCE AND RETREAT ASSIST TOOL OF ENDOSCOPIC TREATMENT INSTRUMENT AND ENDOSCOPIC SYSTEM

(71) Applicant: OLYMPUS MEDICAL SYSTEMS CORP., Tokyo (JP)

(72) Inventors: Tetsuhiro Yamada, Hachioji (JP); Mayumi Shimazaki, Hino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 14/171,396

(22) Filed: Feb. 3, 2014

(65) Prior Publication Data

US 2014/0221739 A1    Aug. 7, 2014

Related U.S. Application Data

(63) Continuation of application No. PCT/JP2013/067859, filed on Jun. 28, 2013.

(30) Foreign Application Priority Data

Jul. 6, 2012   (JP) ................................ 2012-152949

(51) Int. Cl.
| | |
|---|---|
| A61B 1/00 | (2006.01) |
| G02B 23/24 | (2006.01) |
| A61B 17/00 | (2006.01) |
| A61B 1/04 | (2006.01) |
| A61B 1/018 | (2006.01) |

(52) U.S. Cl.
CPC ............ *A61B 1/00133* (2013.01); *G02B 23/24* (2013.01); *A61B 17/00234* (2013.01); *A61B 1/018* (2013.01); *A61B 1/0014* (2013.01)

(58) Field of Classification Search
CPC .................................................. A61B 1/00133
USPC ......... 600/104, 106, 114, 117, 153, 154, 159, 600/123; 348/45
See application file for complete search history.

(56) References Cited

U.S. PATENT DOCUMENTS

| | | | |
|---|---|---|---|
| 7,708,685 B2* | 5/2010 | Okada ........................... | 600/106 |
| 2008/0064920 A1* | 3/2008 | Bakos et al. ................... | 600/102 |

(Continued)

FOREIGN PATENT DOCUMENTS

| | | |
|---|---|---|
| JP | A-09-276212 | 10/1997 |
| JP | A-2003-153907 | 5/2003 |
| JP | A-2003-265406 | 9/2003 |
| JP | A-2007-151595 | 6/2007 |
| JP | A-2008-080119 | 4/2008 |
| JP | A-2011-520480 | 7/2011 |

OTHER PUBLICATIONS

International Search Report issued in International Application No. PCT/JP2013/067859 dated Sep. 17, 2013 (with translation).

(Continued)

*Primary Examiner* — Anhtuan T Nguyen
*Assistant Examiner* — Timothy J Neal
(74) *Attorney, Agent, or Firm* — Oliff PLC

(57) ABSTRACT

An advance and retreat assist tool includes a base unit, a fixing unit and a first tubular member. The advance and retreat assist tool further includes a fixing portion which fixes the treatment instrument to the first tubular member, a rotary portion which provided in the first tubular member and an advance and retreat mechanism which advances and retreats the first tubular member on the basis of the a rotation force of the rotary portion.

16 Claims, 15 Drawing Sheets

(56) References Cited

U.S. PATENT DOCUMENTS

| | | | |
|---|---|---|---|
| 2008/0281153 A1* | 11/2008 | Nakamura et al. | 600/106 |
| 2009/0270677 A1 | 10/2009 | Dillon | |
| 2012/0203064 A1* | 8/2012 | Wynberg | 600/106 |

OTHER PUBLICATIONS

Jan. 15, 2015 International Preliminary Report on Patentability issued in International Application No. PCT/JP2013/067859.

* cited by examiner

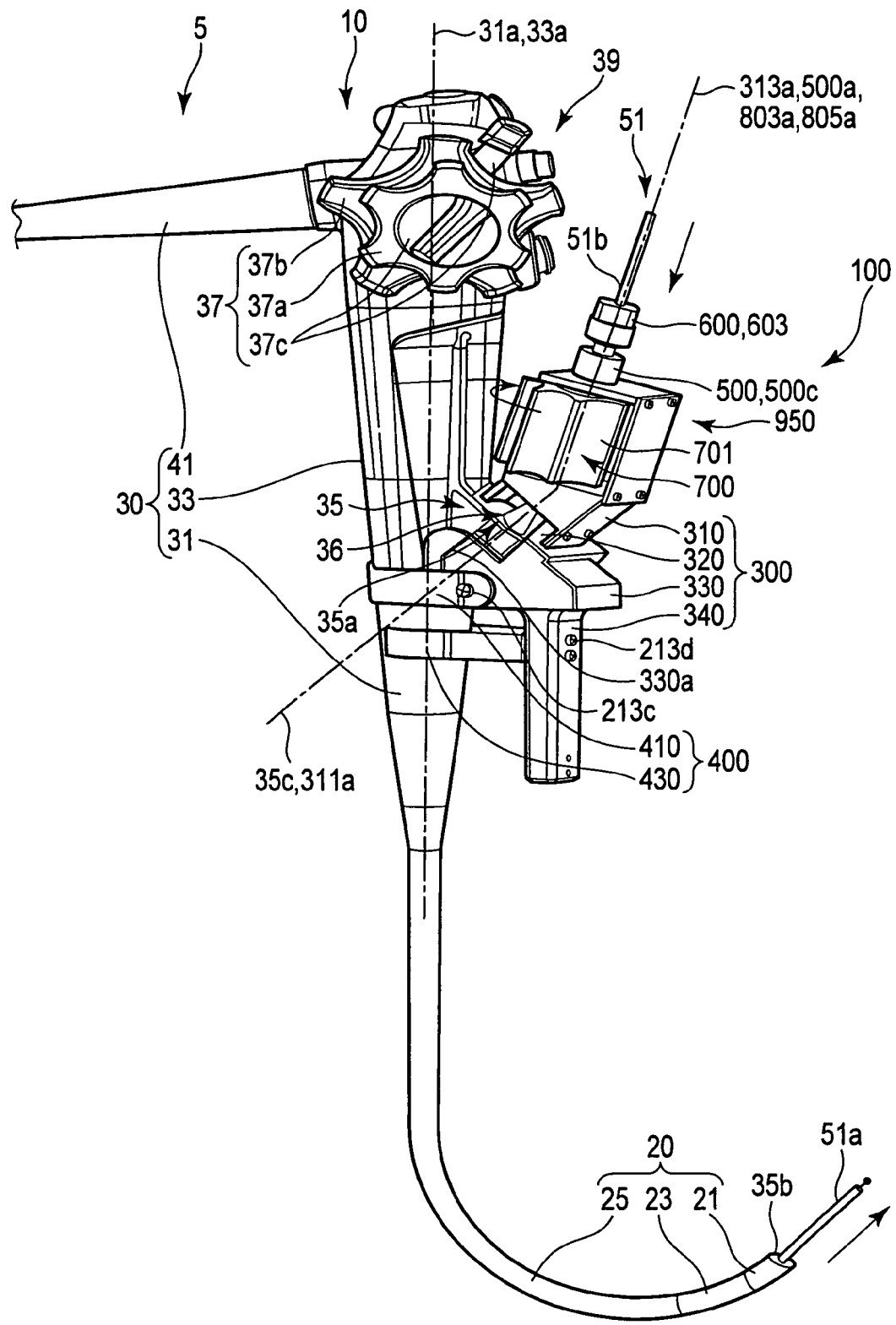
F I G. 1A

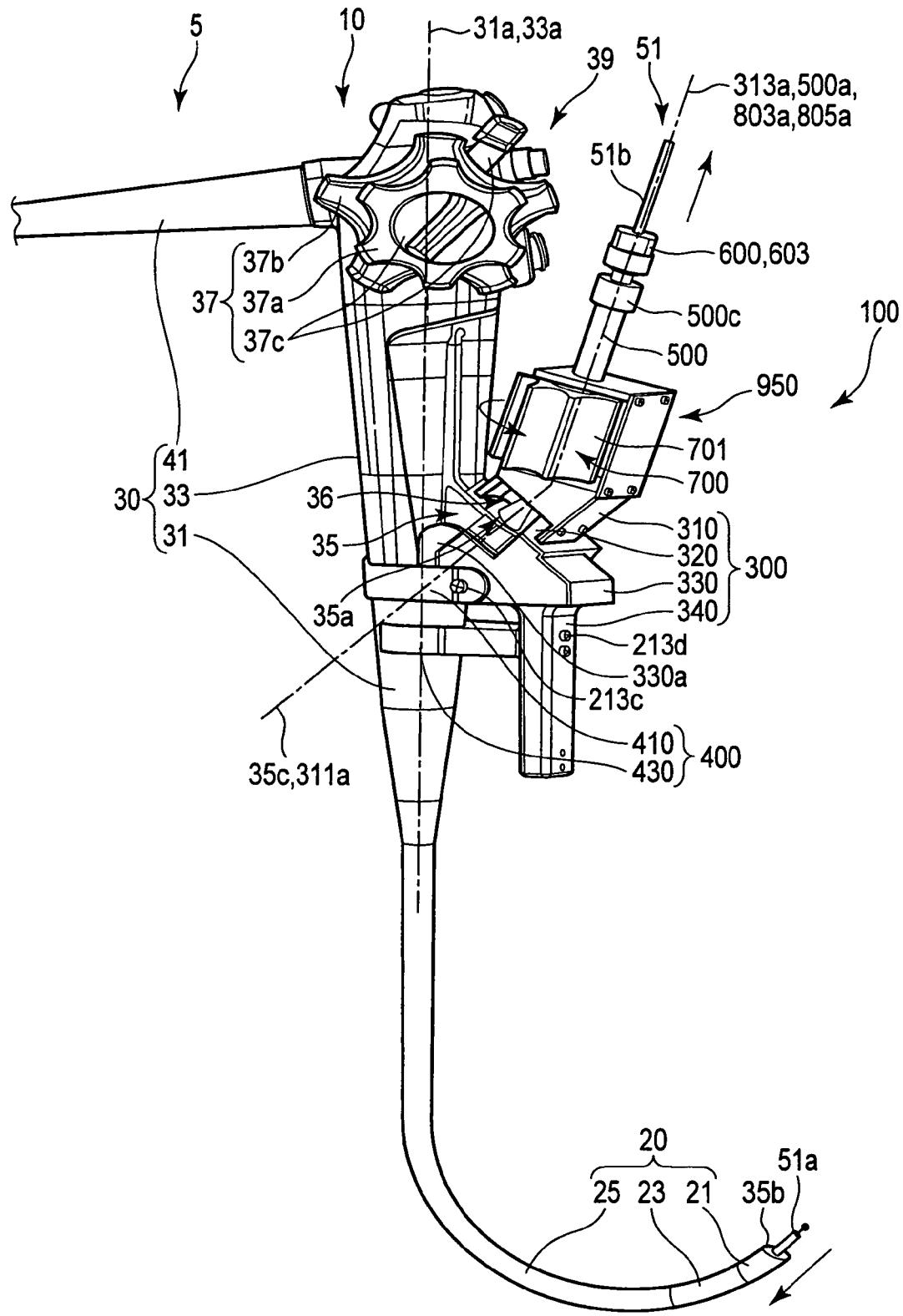
F I G. 1B

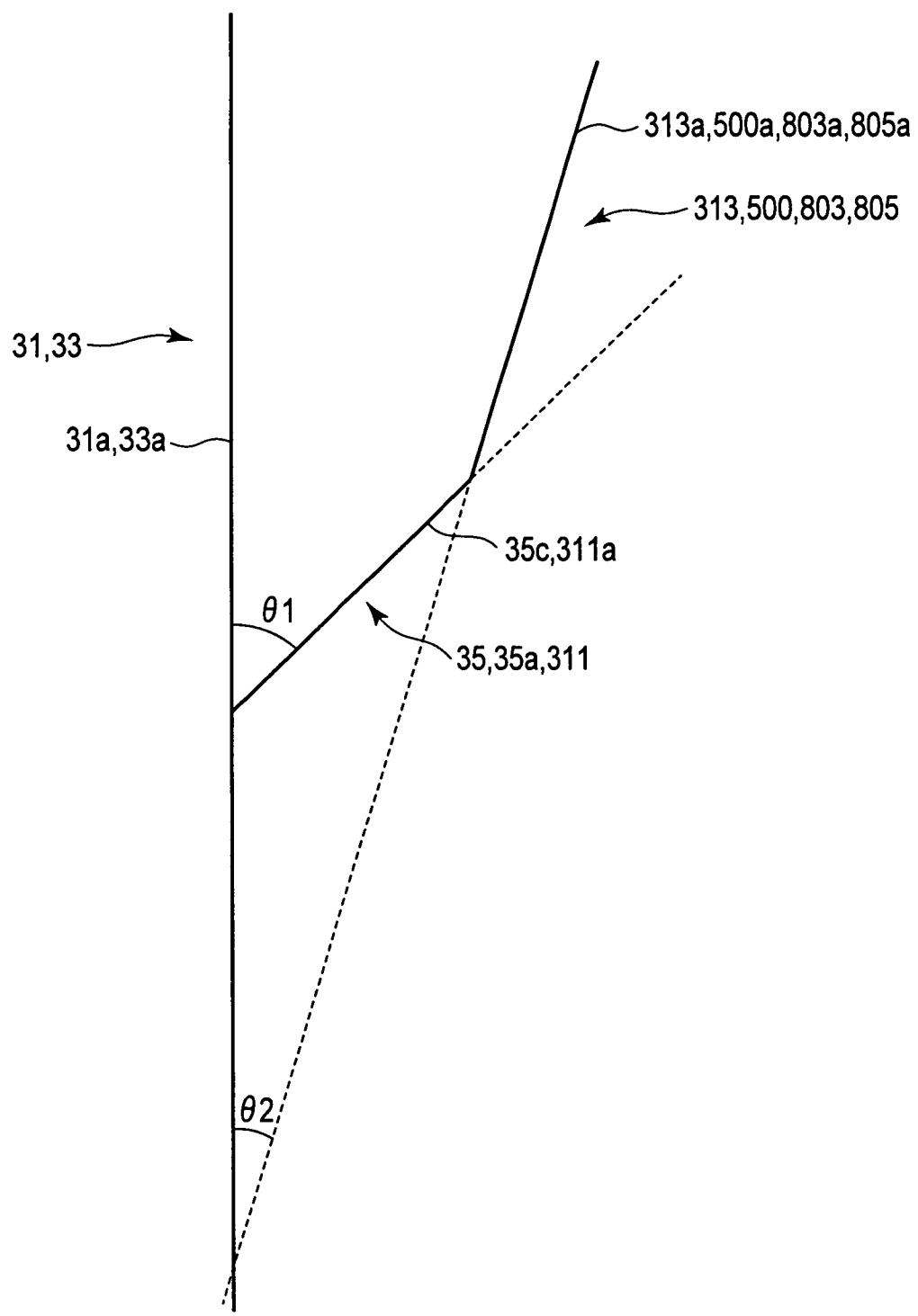
F I G. 1C

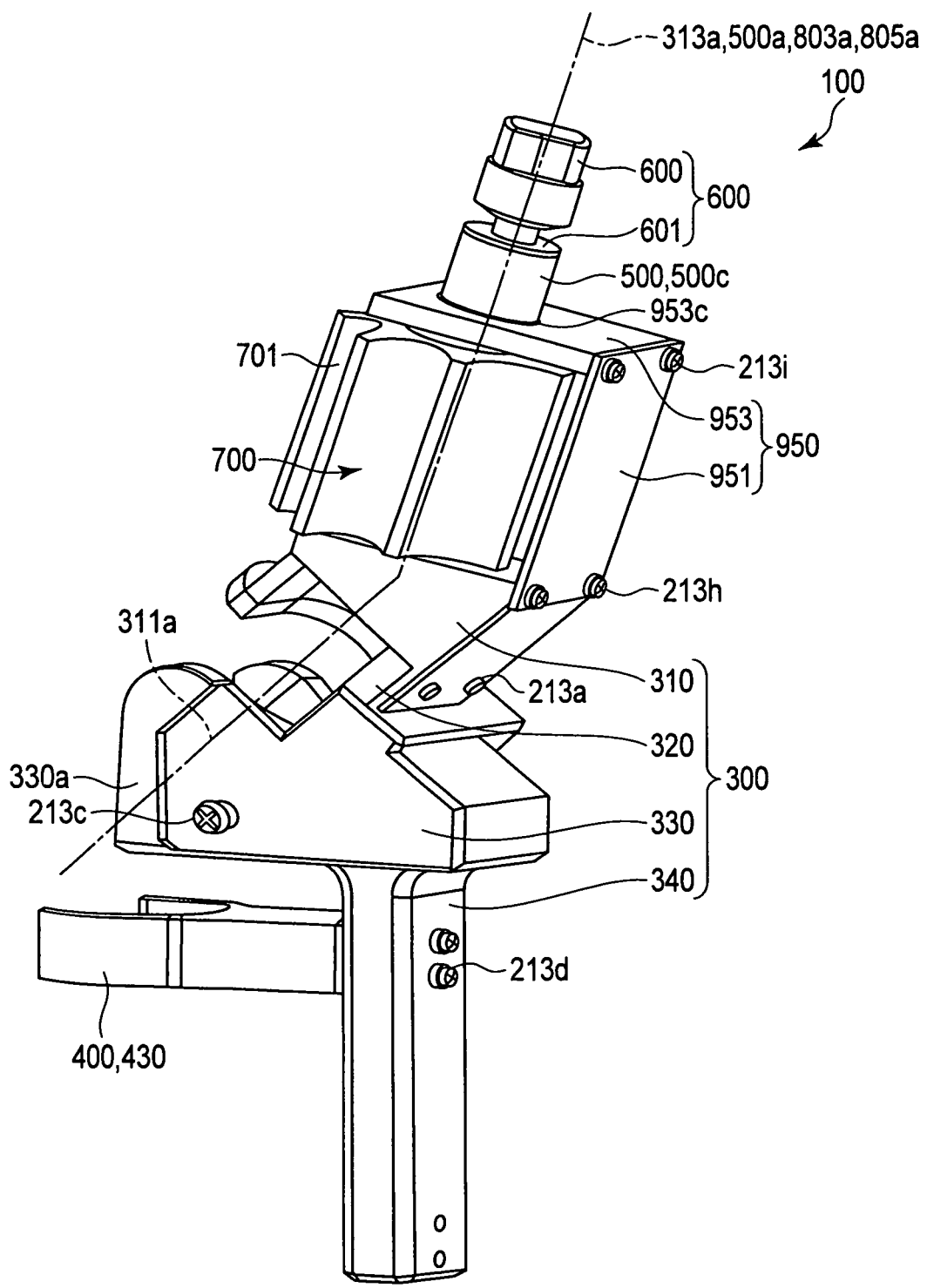
F I G. 2A

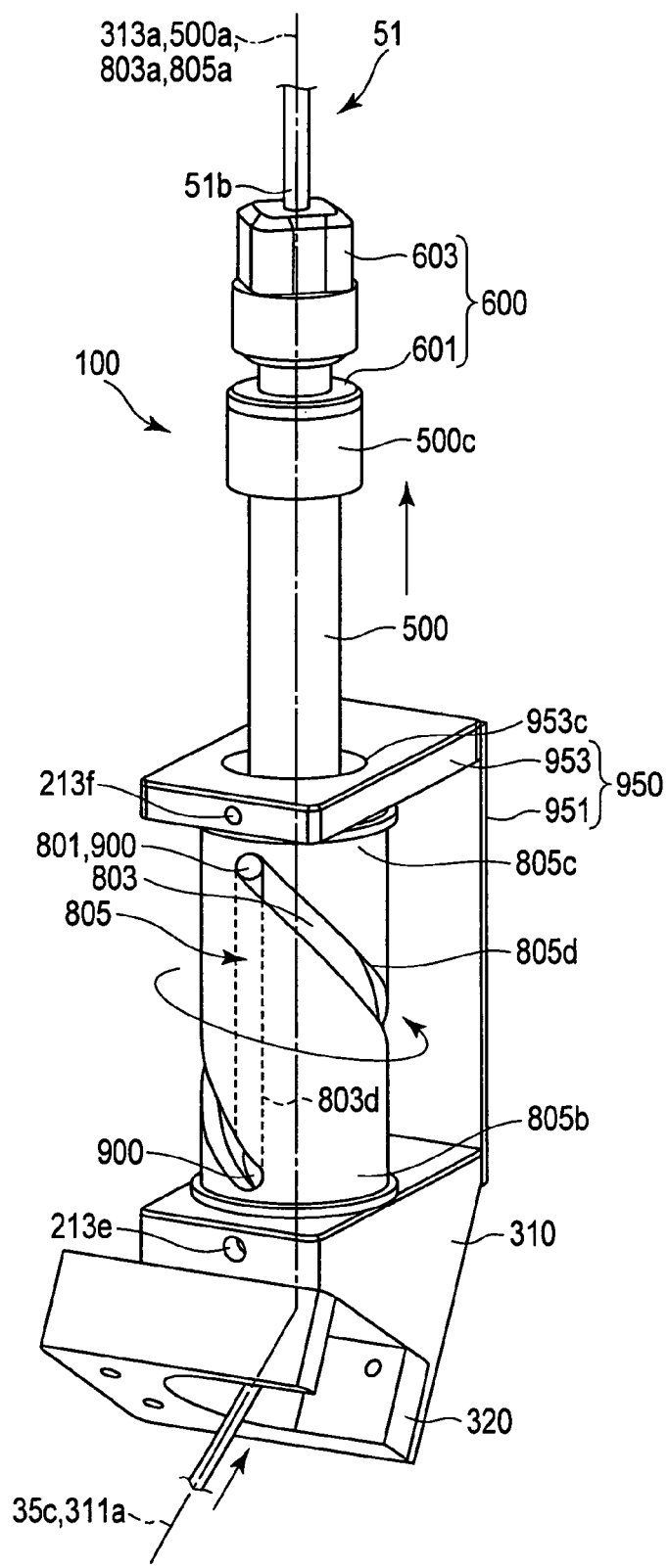
F I G. 3B

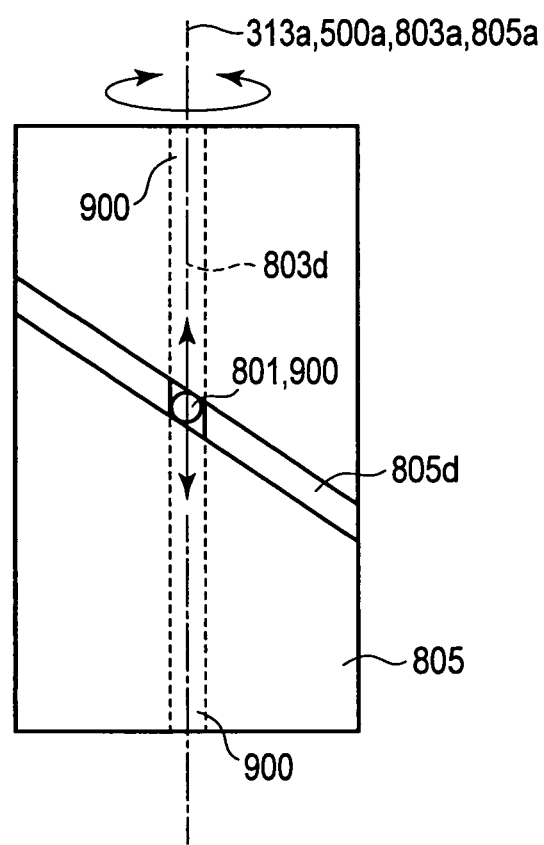
F I G. 3C

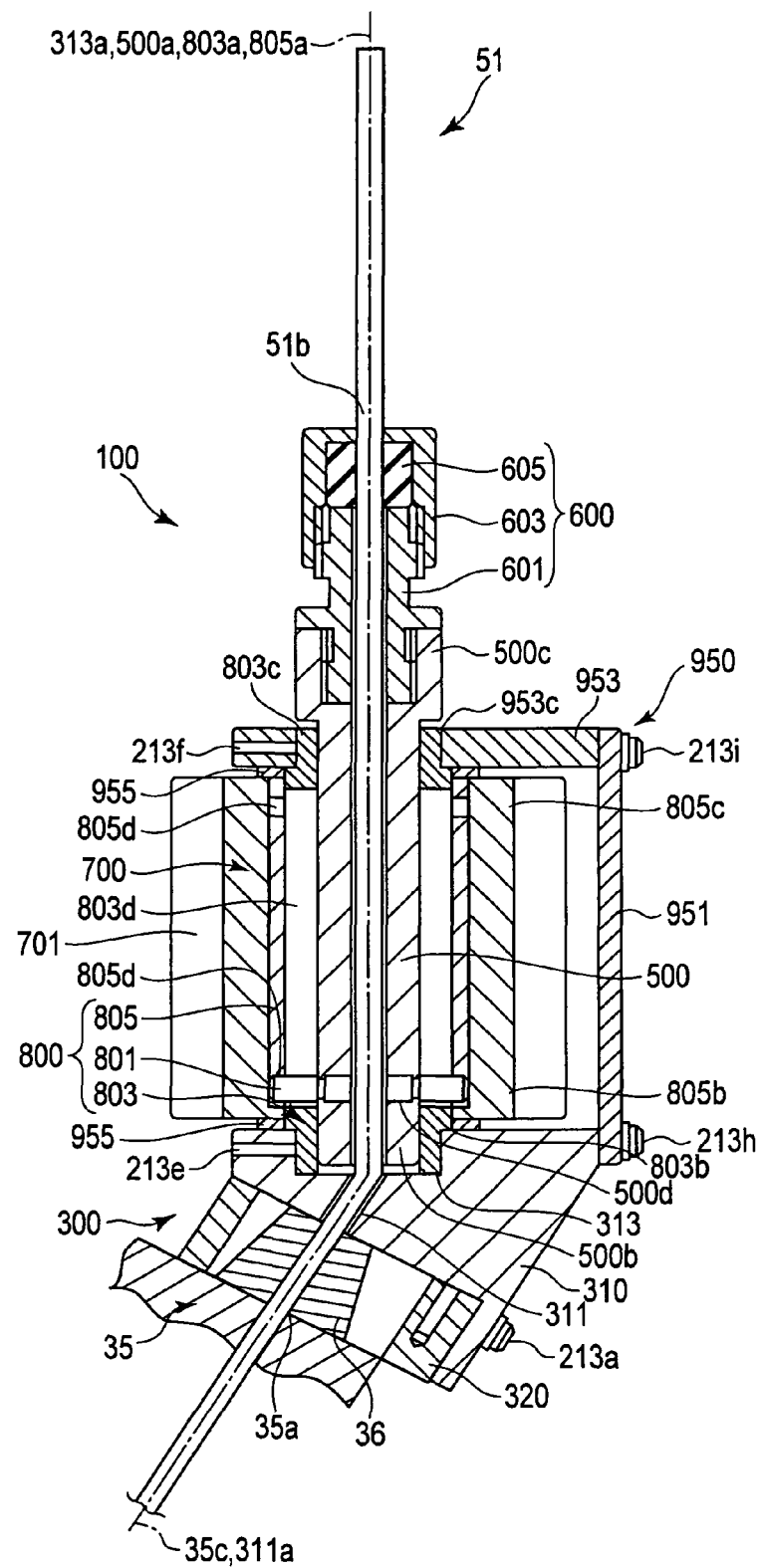
F I G. 4A

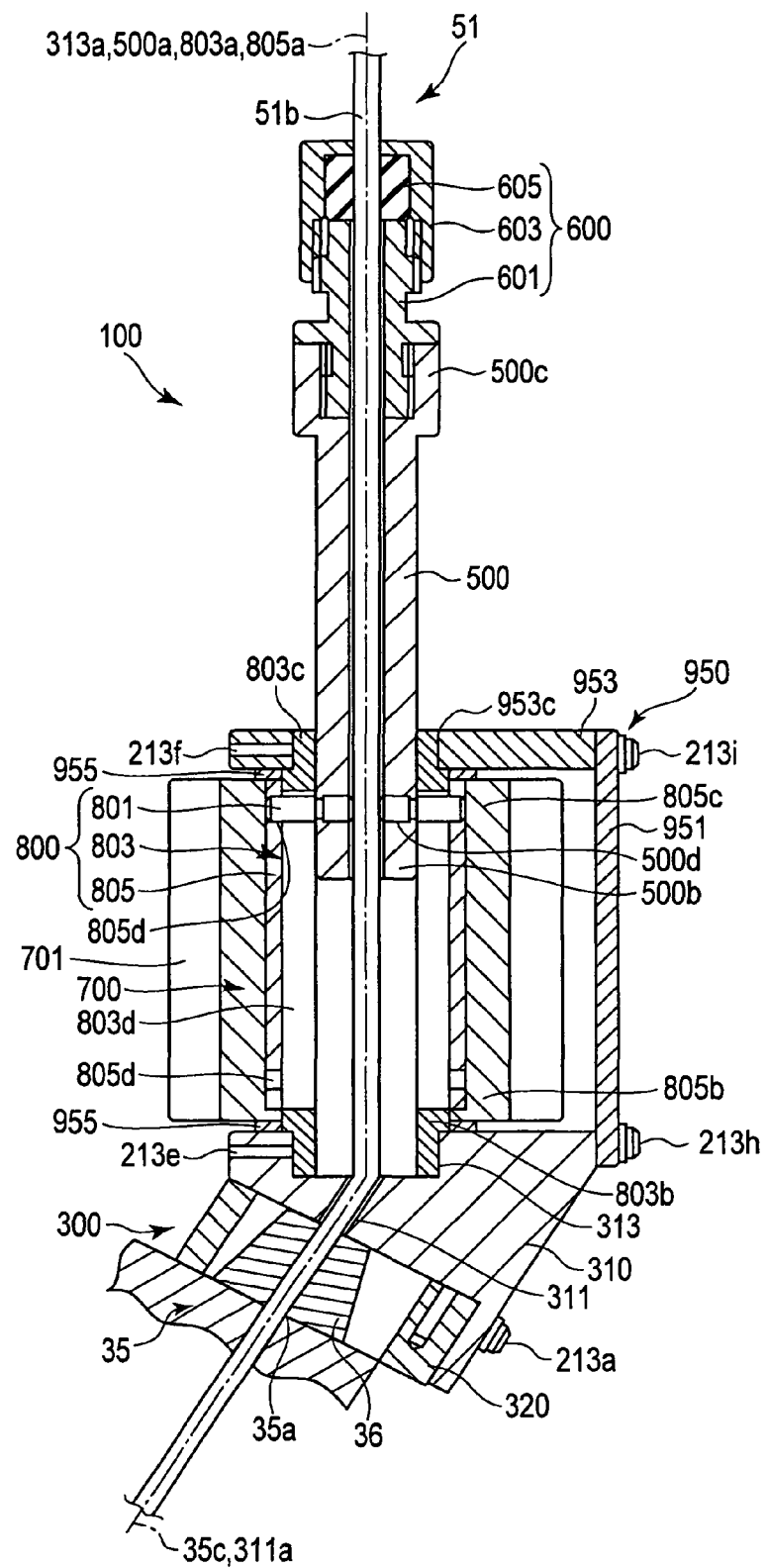
F I G. 4B

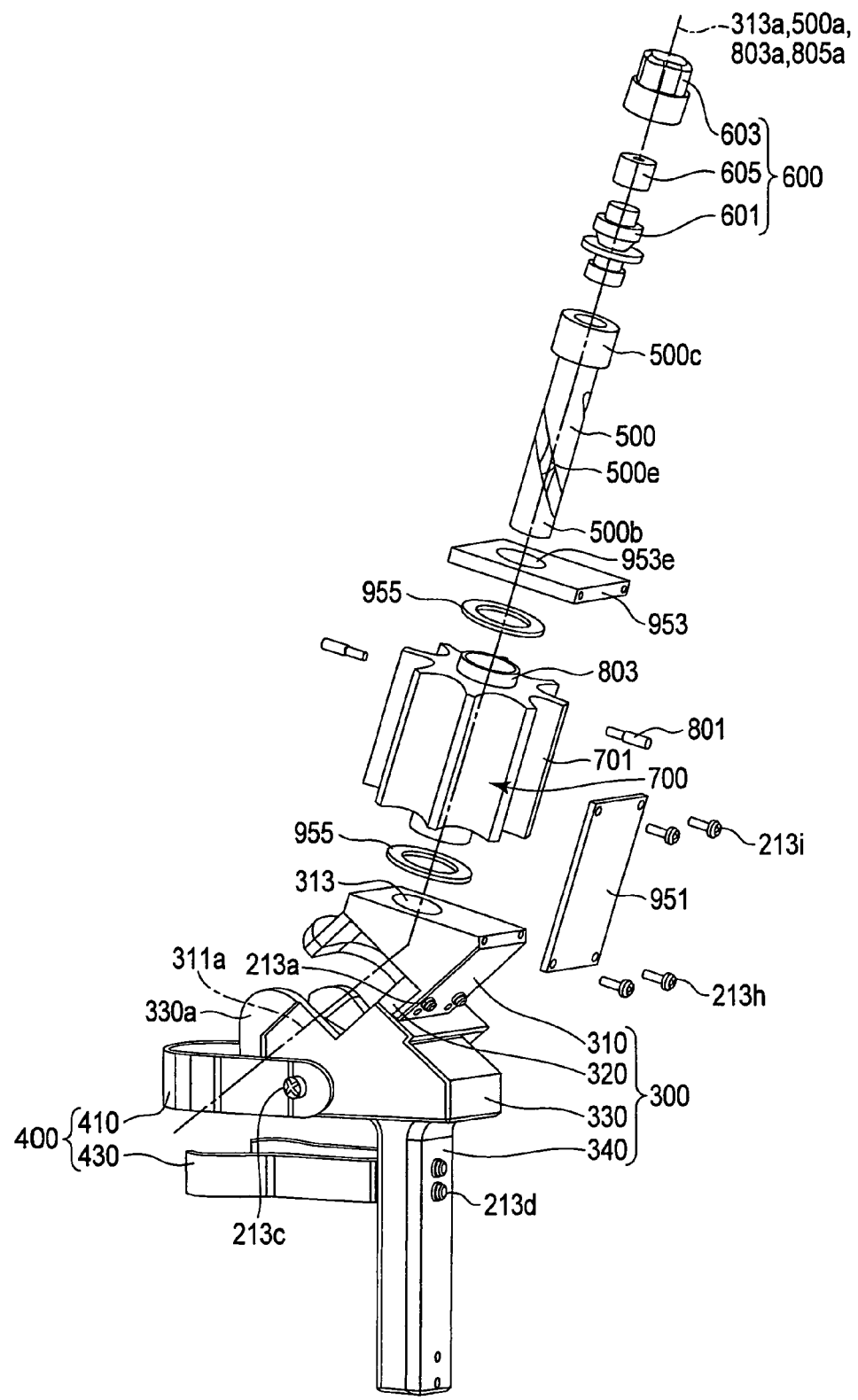
F I G. 6

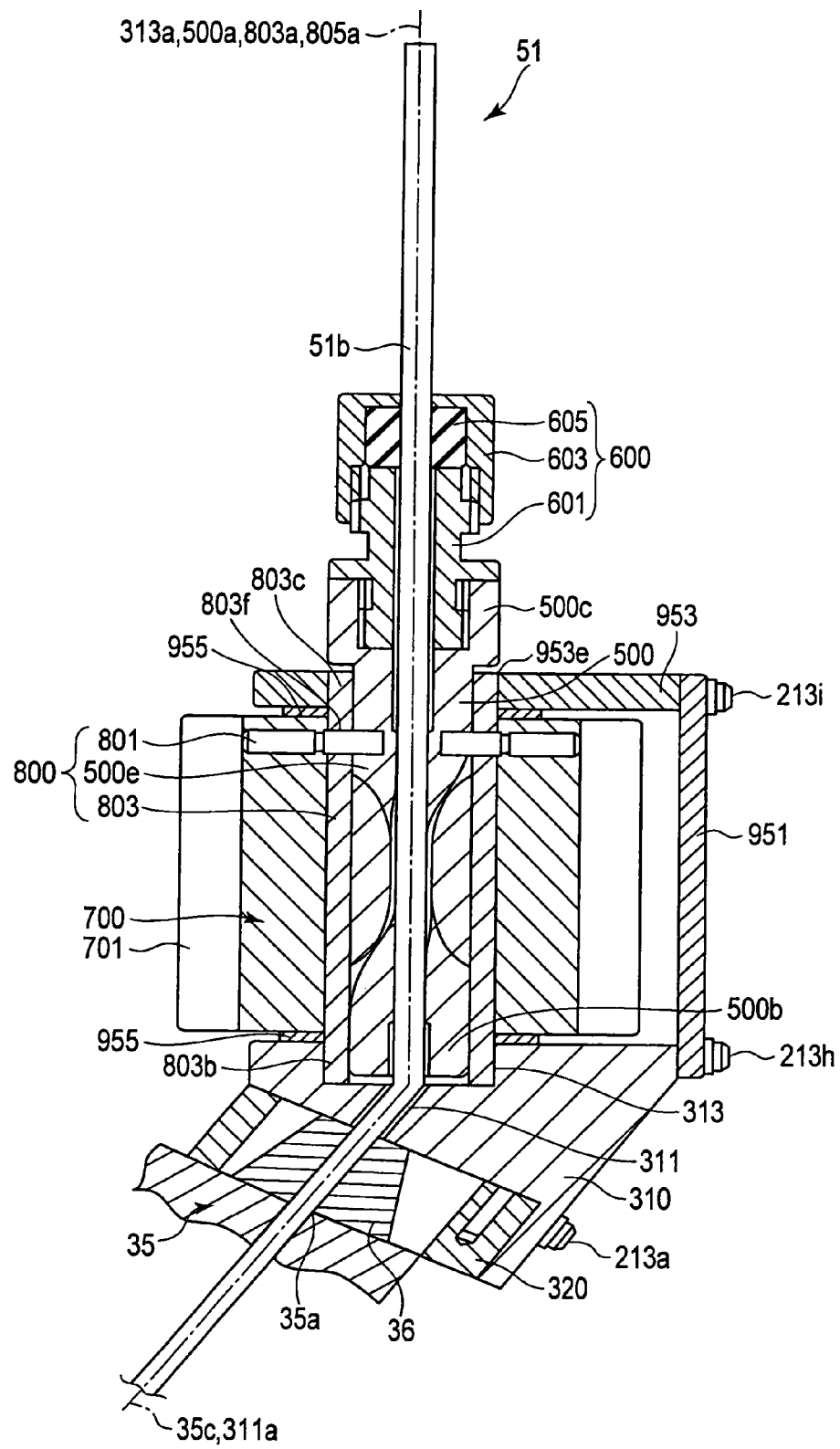
F I G. 7A

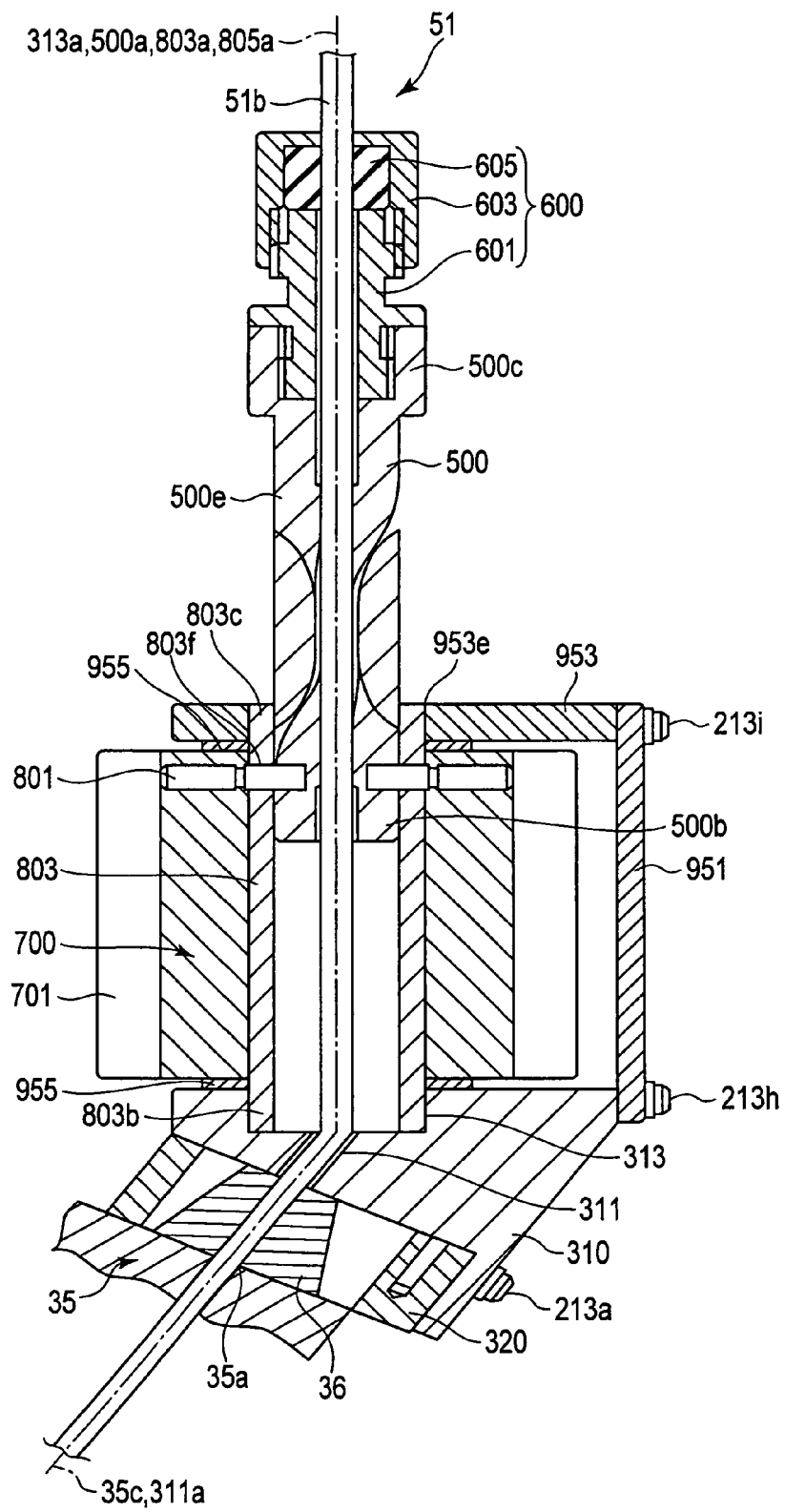
F I G. 7B

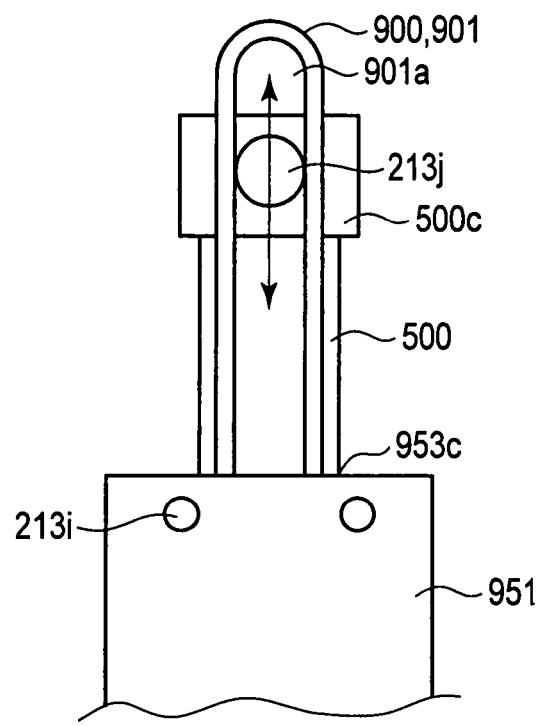
F I G. 8A
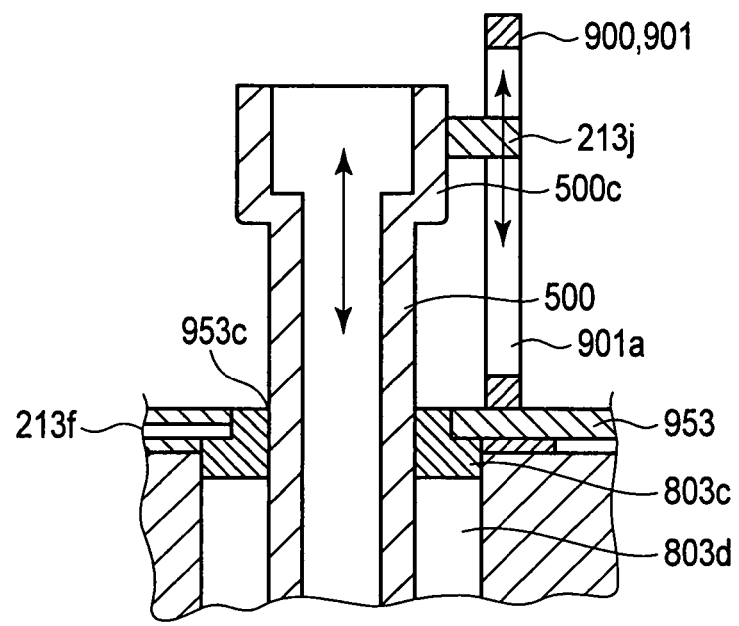
F I G. 8B

ADVANCE AND RETREAT ASSIST TOOL OF ENDOSCOPIC TREATMENT INSTRUMENT AND ENDOSCOPIC SYSTEM

CROSS-REFERENCE TO RELATED APPLICATIONS

This application is a Continuation Application of PCT Application No. PCT/JP2013/067859, filed Jun. 28, 2013 and based upon and claiming the benefit of priority from prior Japanese Patent Application No. 2012-152949, filed Jul. 6, 2012, the entire contents of all of which are incorporated herein by reference.

BACKGROUND OF THE INVENTION

1. Field of the Invention

The present invention relates to an advance and retreat assist tool of an endoscopic treatment instrument, and an endoscopic system having this advance and retreat assist tool.

2. Description of the Related Art

An advance and retreat assist tool of an endoscopic treatment instrument (hereinafter, treatment instrument) assists the treatment instrument in advancing and retreating. Such advance and retreat assist tools have been disclosed in, for example, Jpn. Pat. Appln. KOKAI Publication No. 2007-151595 and Jpn. Pat. Appln. KOKAI Publication No. 9-276212.

For example, in Jpn. Pat. Appln. KOKAI Publication No. 2007-151595, an endoscope has an advance and retreat operation portion provided at the proximal end portion of a grasping portion. The advance and retreat operation portion is provided coaxially with the central axis of the grasping portion. The advance and retreat operation portion has a rotation axis provided in a direction that intersects at right angles with the central axis of the grasping portion. The advance and retreat operation portion rotates around the rotation axis. The advance and retreat operation portion is toothed with the proximal end portion side of the treatment instrument. The advance and retreat operation portion advances and retreats the treatment instrument by the advance and retreat operation portion rotates. The grasping portion is grasped by the left hand of a surgeon, and the advance and retreat operation portion is rotated by the fingers of the left hand of the surgeon.

For example, in Jpn. Pat. Appln. KOKAI Publication No. 9-276212, a medical instrument introduction device is attached to a treatment instrument insertion hole portion so that the medical instrument introduction device is provided straight along the central axis direction of the treatment instrument insertion hole portion of a treatment instrument insertion portion. The central axis direction of the treatment instrument insertion hole portion is slanted relative to the central axis direction of the grasping portion. Thus, the medical instrument introduction device is provided aslant relative to the central axis direction of the grasping portion to depart from the grasping portion. The distal end portion of the medical instrument introduction device is close to the grasping portion, and the proximal end portion of the medical instrument introduction device is located away from the grasping portion.

BRIEF SUMMARY OF THE INVENTION

An aspect of an advance and retreat assist tool of an endoscopic treatment instrument according to the present invention includes a base unit provided in an endoscope including a treatment instrument insertion hole portion into which the endoscopic treatment instrument is inserted, a first tubular member which is provided in the base unit and through which the endoscopic treatment instrument is inserted so that the endoscopic treatment instrument is inserted into the treatment instrument insertion hole portion, a fixing portion which fixes the endoscopic treatment instrument to the first tubular member, a rotary portion including a cylindrical member into which the first tubular member is inserted, the rotary portion rotating around an outer circumference of the first tubular member; and an advance and retreat mechanism which converts a rotation force of the rotary portion to an advance and retreat force to advance and retreat the first tubular member, transmits the advance and retreat force to the first tubular member, and thereby advances and retreats the endoscopic treatment instrument fixed to the first tubular member together with the first tubular member when the rotary portion rotates.

An aspect of an endoscopic system according to the present invention includes an endoscope including a treatment instrument insertion hole portion; the advance and retreat assist tool of the endoscopic treatment instrument provided in the endoscope; and the endoscopic treatment instrument which is inserted into the endoscope from the treatment instrument insertion hole portion and which is assisted by the advance and retreat assist tool in advancing and retreating.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a diagram showing how an advance and retreat assist tool according to a first embodiment of the present invention is attached to an endoscope and how a treatment instrument advances;

FIG. 1B is a diagram showing how the advance and retreat assist tool according to the first embodiment is attached to the endoscope and how the treatment instrument retreats;

FIG. 1C is a diagram showing the relation between an angle θ1 and an angle θ2;

FIG. 2A is a perspective view of the advance and retreat assist tool according to the first embodiment;

FIG. 3B is a perspective view of the advance and retreat assist tool during the retreat of the treatment instrument according to the first embodiment;

FIG. 3C is a front view showing the relation between a protrusion portion, a long opening portion, and a spiral opening portion during the advance and retreat of the treatment instrument according to the first embodiment;

FIG. 4A is a longitudinal sectional view of the advance and retreat assist tool during the advance of the treatment instrument according to the first embodiment;

FIG. 4B is a longitudinal sectional view of the advance and retreat assist tool during the retreat of the treatment instrument according to the first embodiment;

FIG. 6 is an exploded perspective view of the advance and retreat assist tool according to a first modification of the first embodiment;

FIG. 7A is a longitudinal sectional view of the advance and retreat assist tool shown in FIG. 6 during the advance of the treatment instrument;

FIG. 7B is a longitudinal sectional view of the advance and retreat assist tool shown in FIG. 6 during the retreat of the treatment instrument;

FIG. 8A is a front view of a regulating member according to a second modification of the first embodiment; and FIG. 8B is a schematic longitudinal sectional view of the regulating member according to the second modification of the first embodiment.

DETAILED DESCRIPTION OF THE INVENTION

Hereinafter, embodiments of the present invention will be described in detail with reference to the drawings.

[First Embodiment]

[Configuration]

The first embodiment is described with reference to FIG. 1A, FIG. 1B, FIG. 1C, FIG. 2A, FIG. 2B, FIG. 3A, FIG. 3B, FIG. 3C, FIG. 4A, FIG. 4B, and FIG. 5. For example, as a forceps plug 36 is shown in FIG. 1A in a simplified form, some components are not shown for clarity in some of the drawings.

Figure 3A:
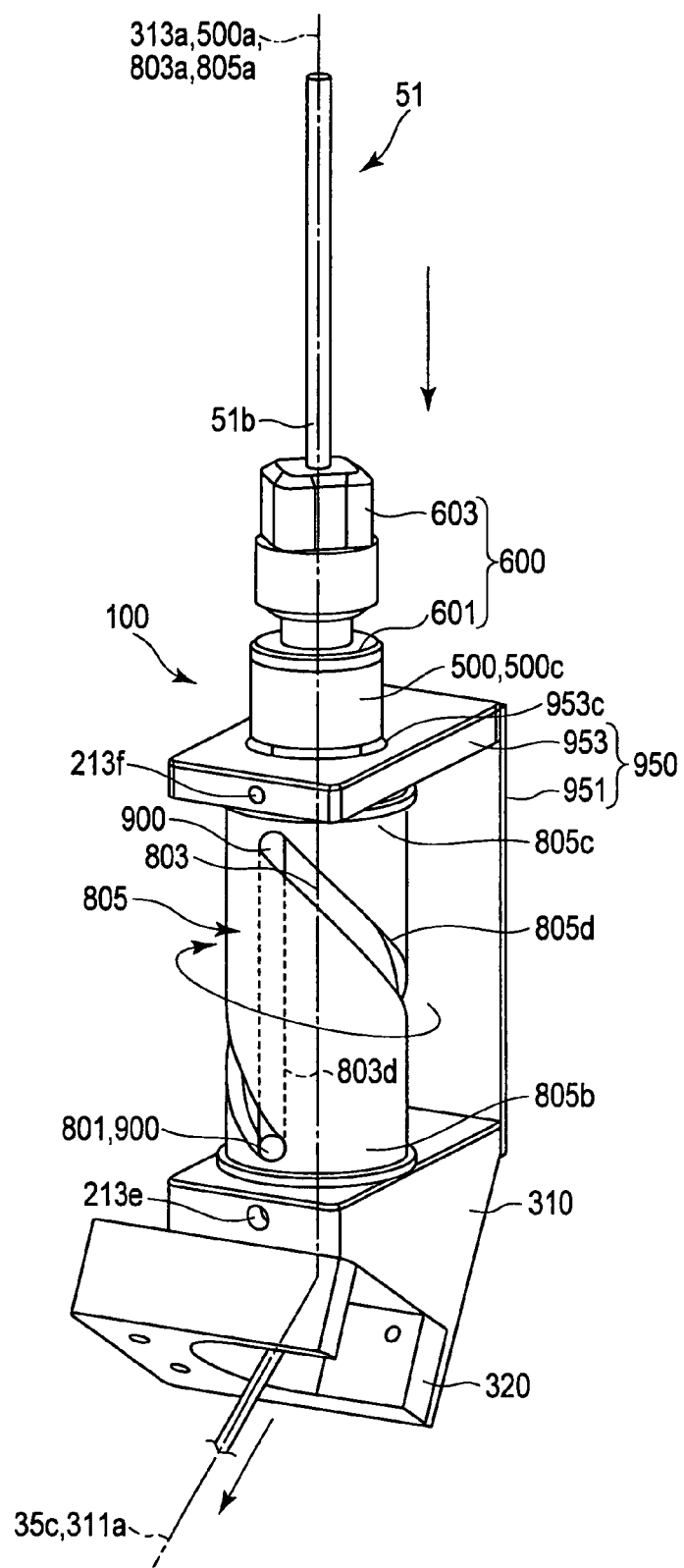
FIG. 3A is a perspective view of the advance and retreat assist tool during the advance of the treatment instrument according to the first embodiment.

As shown in FIG. 1A, FIG. 3A, and FIG. 4A, the advance of a first tubular member 500 means that the first tubular member 500 moves along the direction of a third central axis 500a so that the first tubular member 500 is inserted into a second tubular member 803.

As shown in FIG. 1B, FIG. 3B, and FIG. 4B, the retreat of the first tubular member 500 means that the first tubular member 500 moves along the direction of the third central axis 500a so that the first tubular member 500 is removed from the second tubular member 803.

As shown in FIG. 1A, FIG. 1B, FIG. 3A, FIG. 3B, FIG. 4A, and FIG. 4B, for example, the advance and retreat of the first tubular member 500 includes the advance of the first tubular member 500 and the retreat of the first tubular member 500.

As shown in FIG. 1A, FIG. 3A, and FIG. 4A, for example, the advance of a treatment instrument 51 means that the treatment instrument 51 moves so that the treatment instrument 51 moves to the side of a distal hard portion 21 from the side of an operation portion 30 and a distal end portion 51a of the treatment instrument 51 projects outside from the inside of an insertion portion 20 via a distal opening portion 35b in response to the advance of the first tubular member 500.

As shown in FIG. 1B, FIG. 3B, and FIG. 4B, for example, the retreat of the treatment instrument 51 means that the treatment instrument 51 moves so that the treatment instrument 51 moves to the side of an operation portion 30 from the side of the distal hard portion 21 and the distal end portion 51a of the treatment instrument 51 is housed in the insertion portion 20 from the outside via the distal opening portion 35b in response to the retreat of the first tubular member 500.

As shown in FIG. 1A, FIG. 1B, FIG. 3A, FIG. 3B, FIG. 4A, and FIG. 4B, for example, the advance and retreat of the treatment instrument 51 includes the advance of the treatment instrument 51 and the retreat of the treatment instrument 51.

[Endoscopic System 5]

As shown in FIG. 1A and FIG. 1B, an endoscopic system 5 has an endoscope 10, the endoscopic treatment instrument (hereinafter, treatment instrument 51), and an advance and retreat assist tool 100 of the treatment instrument 51.

[Endoscope 10]

The endoscope 10 has a hollow and elongated insertion portion 20 to be inserted into, for example, a body cavity, and the operation portion 30 which is coupled to the proximal end portion of the insertion portion 20 and which operates the endoscope 10.

[Insertion Portion 20]

The insertion portion 20 has the distal hard portion 21, a bending portion 23, and a flexible tubular portion 25 from the distal end portion side of the insertion portion 20 to the proximal end portion side of the insertion portion 20. The proximal end portion of the distal hard portion 21 is coupled to the distal end portion of the bending portion 23, and the proximal end portion of the bending portion 23 is coupled to the distal end portion of the flexible tubular portion 25.

The distal hard portion 21 is the distal end portion of the insertion portion 20, and is hard and unbendable. The distal hard portion 21 has the distal opening portion 35b, an unshown observation window included in an unshown observation optical system, an unshown pair of illumination windows which are provided across the observation window and which are included in an unshown illumination optical system, and a nozzle which supplies air and water to the observation window. The distal opening portion 35b, the observation window, the illumination windows, and the nozzle are provided in the distal face of the distal hard portion 21.

The bending portion 23 is bent in a desired direction, for example, in an upward, downward, leftward, or rightward direction by the operation of a later-described bending operation portion 37. When the bending portion 23 is bent, the position and direction of the distal hard portion 21 are changed, an observation target is illuminated by unshown illumination light, and the observation target enters into an observation field. This observation target is, for example, an affected part or a lesion in a subject (e.g., body cavity).

The flexible tubular portion 25 has desired flexibility. Therefore, the flexible tubular portion 25 is bent by an external force. The flexible tubular portion 25 is a tubular member extending from a later-described body portion 31 in the operation portion 30.

[Operation Portion 30]

The operation portion 30 has the body portion 31 from which the flexible tubular portion 25 extends, a grasping portion 33 which is coupled to the proximal end portion of the body portion 31 and which is grasped by a surgeon who operates the endoscope 10, and a universal cord 41 connected to the grasping portion 33.

[Grasping Portion 33]

Figure 5:
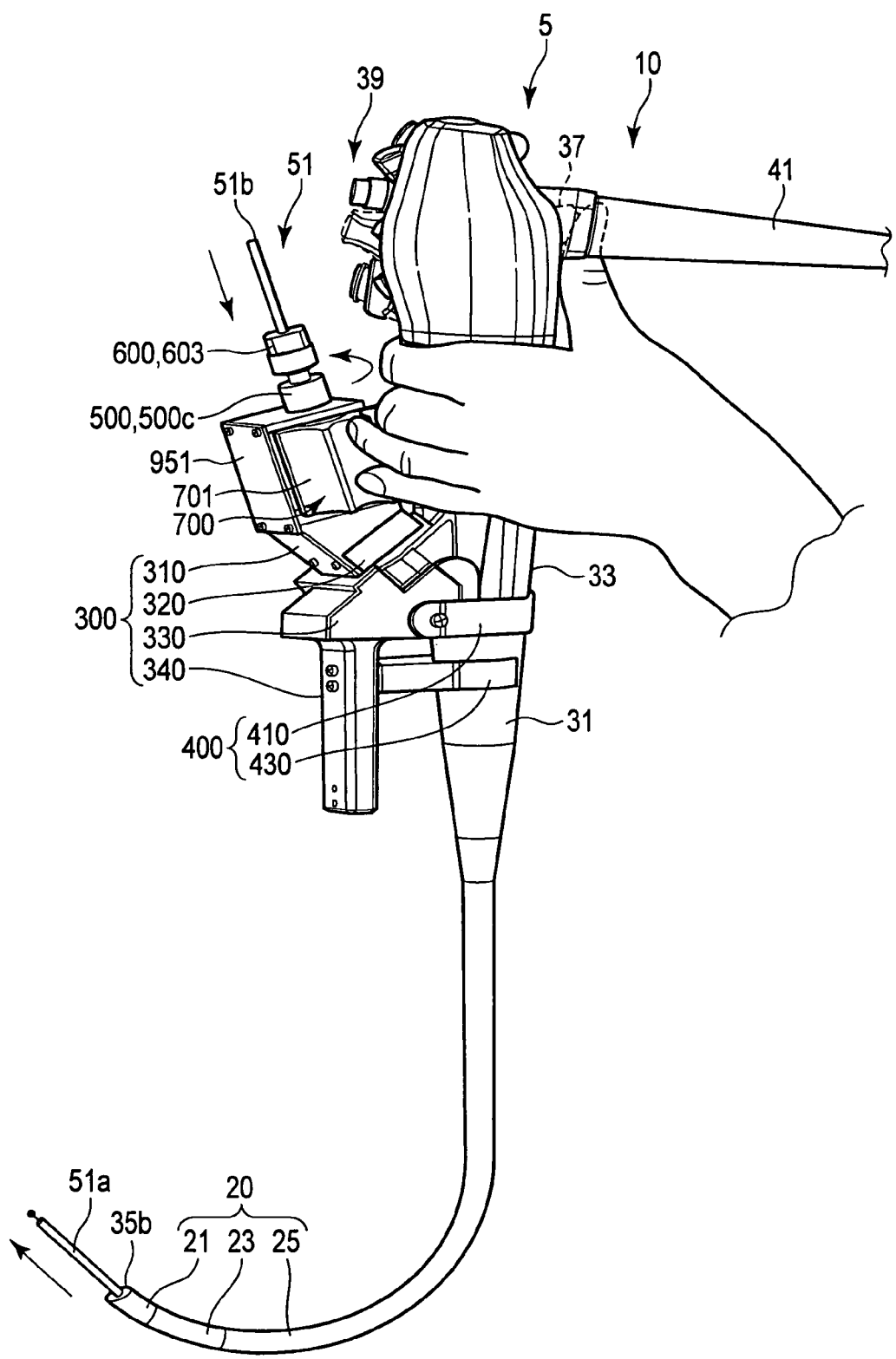
FIG. 5 is a diagram showing how a bending operation portion and a rotation portion are operated by the fingers of the left hand of a surgeon while a grasping portion is being grasped by the left hand in the endoscope to which the advance and retreat assist tool is attached according to the first embodiment.

The grasping portion 33 has a treatment instrument insertion portion 35, the bending operation portion 37 which is operated to bend the bending portion 23, and a switch portion 39. The treatment instrument insertion portion 35 is provided on the distal end portion side of the grasping portion 33. The bending operation portion 37 and the switch portion 39 are provided on the proximal end portion side of the grasping portion 33. As shown in FIG. 5, the grasping portion 33 is grasped by the left hand of the surgeon, and the bending operation portion 37 and the switch portion 39 are operated by the fingers of the left hand.

[Treatment Instrument Insertion Portion 35]

The treatment instrument insertion portion 35 branches off from the grasping portion 33. Thus, as shown in FIG. 1A and FIG. 1B, the central axis direction of the treatment instrument insertion portion 35 is slanted relative to the direction of a central axis 33a of the grasping portion 33.

As shown in FIG. 1A and FIG. 1B, the treatment instrument insertion portion 35 has a treatment instrument insertion hole portion 35a which is provided at the end portion of the treatment instrument insertion portion 35 and which is used to insert the treatment instrument 51 into the endoscope 10.

The treatment instrument insertion hole portion 35a is coupled to the proximal end portion of an unshown treatment instrument insertion channel. The treatment instrument insertion channel is provided inside the insertion portion 20, and provided from the flexible tubular portion 25 to the distal hard portion 21 via the bending portion 23. The distal end portion of the treatment instrument insertion channel is in communication with the distal opening portion 35b provided in the distal hard portion 21. The treatment instrument insertion hole portion 35a is an insertion hole portion used to insert the treatment instrument 51 into the treatment instrument insertion channel. The treatment instrument 51 is inserted into the treatment instrument insertion channel from the treatment instrument insertion hole portion 35a, and pressed to the side of the distal hard portion 21. The treatment instrument 51 is then projected from the distal opening portion 35b.

As shown in FIG. 1A and FIG. 1B, a central axis 35c of the treatment instrument insertion hole portion 35a is provided coaxially with the central axis of the treatment instrument insertion portion 35. Thus, the central axis 35c is slanted relative to the central axis 33a of the grasping portion 33. The direction of the central axis 35c is slanted relative to the direction of the central axis 33a of the grasping portion 33.

As shown in FIG. 1A, FIG. 1B, FIG. 4A, and FIG. 4B, the treatment instrument insertion portion 35 further has the cylindrical forceps plug 36 to be inserted into the treatment instrument insertion hole portion 35a. The forceps plug 36 is made of, for example, a metal. The central axis of the forceps plug 36 is provided coaxially with the central axis 35c of the treatment instrument insertion hole portion 35a. Thus, the forceps plug 36 is slanted relative to the grasping portion 33. When the cylindrical forceps plug 36 is disposed in the treatment instrument insertion hole portion 35a, the forceps plug 36 is in communication with the treatment instrument insertion channel.

The treatment instrument 51 is inserted into the treatment instrument insertion channel from the treatment instrument insertion hole portion 35a via the forceps plug 36, and pressed to the side of the distal hard portion 21. As shown in FIG. 1A and FIG. 1B, the treatment instrument 51 is then projected from the distal opening portion 35b.

As shown in FIG. 1A, FIG. 1B, FIG. 4A, and FIG. 4B, the forceps plug 36 is surrounded by a later-described base member 32, and is in communication with a first hole portion 311 of a later-described base member 310. The forceps plug 36 is in communication with the treatment instrument insertion hole portion 35a, and is mounted on the treatment instrument insertion portion 35 to be provided flush with the treatment instrument insertion hole portion 35a.

[Bending Operation Portion 37]

The bending operation portion 37 has a horizontal bending operation knob 37a which is operated to horizontally bend the bending portion 23, a vertical bending operation knob 37b which is operated to vertically bend the bending portion 23, and a fixing knob 37c which fixes the position of the curved bending portion 23.

[Switch Portion 39]

The switch portion 39 is operated by the hand of the surgeon when the grasping portion 33 is grasped by the surgeon. The switch portion 39 is operated during the operation of various functions of the endoscope such as air supply, water supply, suction, and photography.

[Universal Cord 41]

The universal cord 41 has an unshown connector which can be attached to and removed from an unshown control apparatus.

[Treatment Instrument 51]

The treatment instrument 51 is formed by an elongated linear member, for example.

[Advance and Retreat Assist Tool 100]

As shown in FIG. 1A and FIG. 1B, the advance and retreat assist tool 100 is removably attached to the endoscope 10 around the treatment instrument insertion hole portion 35a. The advance and retreat assist tool 100 is attached to, for example, the treatment instrument insertion portion 35, the grasping portion 33, and the body portion 31. The advance and retreat assist tool 100 assists the treatment instrument 51 including the distal end portion 51a of the treatment instrument 51 in advancing and retreating along a longitudinal axis direction of the treatment instrument 51. The treatment instrument 51 is inserted in the endoscope 10 from the forceps plug 36 via the treatment instrument insertion hole portion 35a, and projects from the distal opening portion 35b.

As shown in FIG. 1A and FIG. 1B, the advance and retreat assist tool 100 has a base unit 300, and a fixing unit 400 which fixes the base unit 300 to the endoscope 10. As shown in FIG. 1A and FIG. 1B, the advance and retreat assist tool 100 further has the first tubular member 500 through which the treatment instrument 51 is inserted and which guides the treatment instrument 51 to the endoscope 10 via the base unit 300, and a fixing portion 600 which fixes the treatment instrument 51 to the first tubular member 500. As shown in FIG. 1A, FIG. 1B, FIG. 2A, FIG. 2B, FIG. 3A, FIG. 3B, FIG. 3C, FIG. 4A, and FIG. 4B, the advance and retreat assist tool 100 further has a rotary portion 700 provided in the first tubular member 500, and an advance and retreat mechanism 800 which advances and retreats the first tubular member 500 by a rotation force of the rotary portion 700. The advance and retreat assist tool 100 further has a regulating mechanism 900 which regulates the advance and retreat of the first tubular member 500, and a support unit 950 which supports the first tubular member 500 so that the first tubular member 500 advances and retreats.

[Base Unit 300]

Figure 2B:
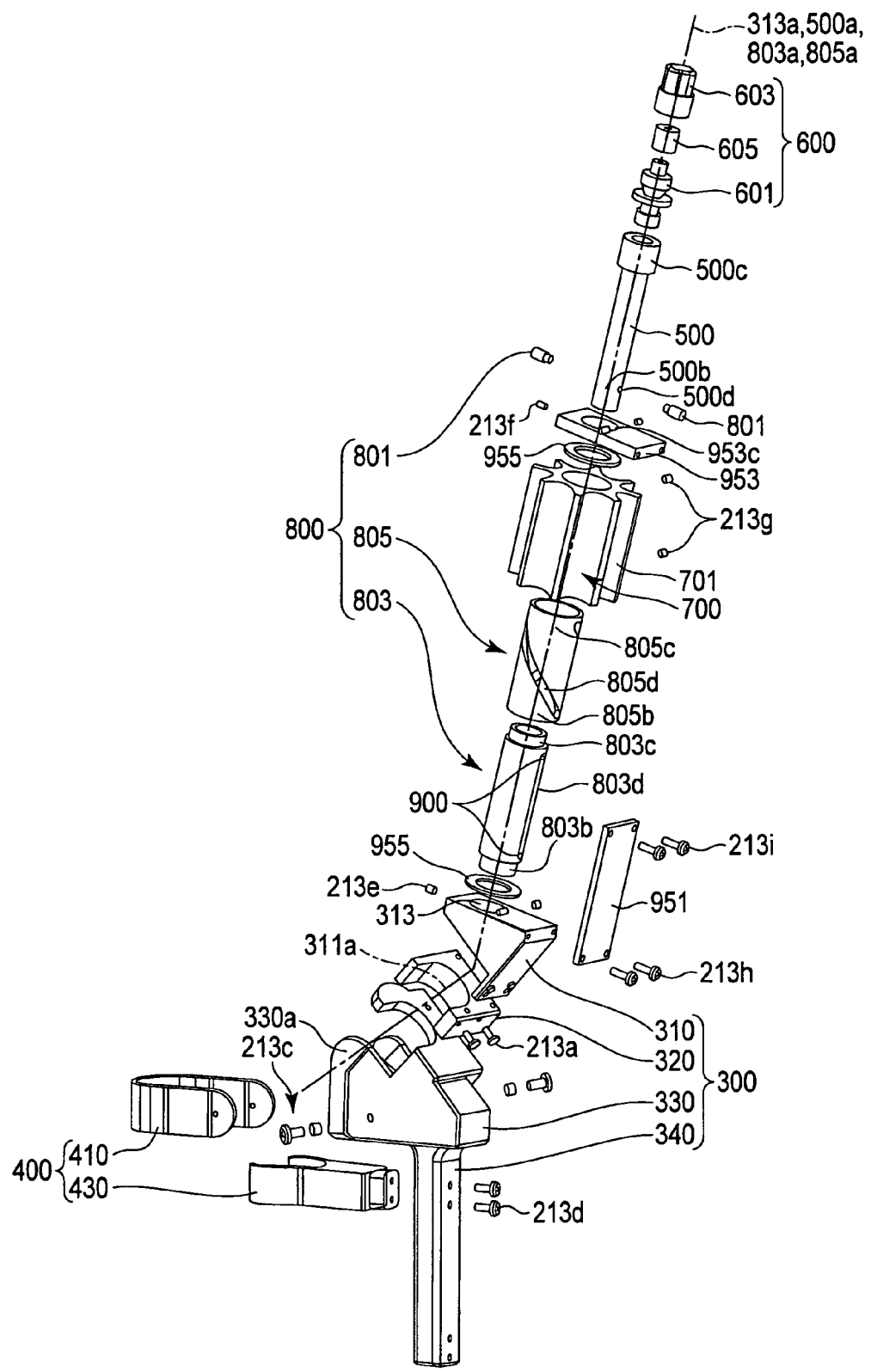
FIG. 2B is an exploded perspective view of the advance and retreat assist tool according to the first embodiment.

As shown in FIG. 1A, FIG. 1B, FIG. 2A, FIG. 2B, FIG. 3A, FIG. 3B, FIG. 4A, and FIG. 4B, the base unit 300 is removably attached to the treatment instrument insertion portion 35, the grasping portion 33, and the body portion 31 around the treatment instrument insertion hole portion 35a including the forceps plug 36. As shown in FIG. 2A and FIG. 2B, the base unit 300 has the substantially triangular-prism-shaped base member 310, and a U-shaped base member 320. The base unit 300 further has a support member 330 which supports the base member 310 via the base member 320, and an extension member 340 extending from the support member 330 toward side of the insertion portion 20.

As shown in FIG. 1A and FIG. 1B, the base member 310 and the base member 320 are disposed on the side of the treatment instrument insertion hole portion 35a to surround the forceps plug 36 when the advance and retreat assist tool 100 is attached to the endoscope 10.

As shown in FIG. 1A and FIG. 1B, the support member 330 is disposed on the side of the grasping portion 33 when the advance and retreat assist tool 100 is attached to the endoscope 10.

As shown in FIG. 1A and FIG. 1B, the extension member 340 is disposed on the side of the body portion 31 when the advance and retreat assist tool 100 is attached to the endoscope 10.

[Base Member 310]

As shown in FIG. 4A, and FIG. 4B, the base member 310 has the first hole portion 311 having a first central axis 311a, and a second hole portion 313 which has a second central axis 313a slanted relative to the first central axis 311a and which is in communication with the first hole portion 311.

The first hole portion 311 faces the treatment instrument insertion hole portion 35a and the treatment instrument insertion channel when the advance and retreat assist tool 100 is attached to the endoscope 10. At the same time, as shown in FIG. 1A, FIG. 1B, and FIG. 1C, the first central axis 311a of the first hole portion 311 is provided coaxially with the central axis 35c of the treatment instrument insertion hole portion 35a, and is slanted relative to the direction of the central axis 33a of the grasping portion 33. As shown in FIG. 10, the second central axis 313a of the second hole portion 313 is slanted toward the central axis 33a of the grasping portion 33 relative to the central axis 35c of the treatment instrument insertion hole portion 35a.

As shown in FIG. 10, an angle formed between the direction of the central axis 35c of the treatment instrument insertion hole portion 35a (the direction of the first central axis 311a of the first hole portion 311) and the direction of the central axis 33a of the grasping portion 33 is an angle $\theta 1$.

As shown in FIG. 10, an angle formed between the direction of the second central axis 313a and the direction of the central axis 33a of the grasping portion 33 is an angle $\theta 2$.

In this case, the angle $\theta 1 >$ the angle $\theta 2$. The angle $\theta 1$ and the angle $\theta 2$ are fixed, and the relation of the angle $\theta 1 >$ the angle $\theta 2$ is constantly maintained.

The first hole portion 311 is in communication with the outside in one end face of the base member 310, and the second hole portion 313 is in communication with the outside in the other end face of the base member 310. The second hole portion 313 is recessed in the other end face of the base member 310.

As shown in FIG. 4A, and FIG. 4B, the first hole portion 311 and the second hole portion 313 function as guide hole portions to guide the treatment instrument 51 which is inserted through the first tubular member 500 to the treatment instrument insertion hole portion 35a. The second hole portion 313 also functions as an insertion hole portion in which the first tubular member 500 is inserted.

As shown in FIG. 2A and FIG. 2B, the base member 310 is fixed to the base member 320 by, for example, a screw portion 213a.

[Base Member 320]

As shown in FIG. 2A and FIG. 2B, the base member 320 is fixed to the base member 310 by, for example, the screw portion 213a, and is fixed to the support member 330 by an unshown screw portion. The base member 320 is mounted on the treatment instrument insertion portion 35.

The inner circumferential surface of the base member 320 is formed along the shape of the forceps plug 36, and is provided along the circumference of the central axis of the forceps plug 36. An inner circumferential surface is, for example, substantially U-shaped. In the base member 320 having such the inner circumferential surface, the forceps plug 36 is fitted into the base member 320 so that the first central axis 311a is provided coaxially with the central axis of the forceps plug 36. The height of the base member 310 is substantially the same as the projection amount of the forceps plug 36 projecting from the treatment instrument insertion hole portion 35a.

[Support Member 330]

As shown in FIG. 2A and FIG. 2B, the support member 330 has a displacement prevention portion 330a which pinches, for example, the treatment instrument insertion portion 35 and thereby prevents the displacement of the base unit 300 including the support member 330 when the advance and retreat assist tool 100 is attached to the endoscope 10. As shown in FIG. 1A, FIG. 1B, FIG. 2A, FIG. 2B, FIG. 4A, and FIG. 4B, the displacement prevention portion 330a prevents the displacement of the base unit 300 so that the support member 330 is provided on the side of the grasping portion 33, the extension member 340 is provided on the side of the body portion 31, the first hole portion 311 faces the treatment instrument insertion hole portion 35a, and the first central axis 311a is provided coaxially with the central axis 35c of the treatment instrument insertion hole portion 35a when the advance and retreat assist tool 100 is attached to the endoscope 10. The displacement prevention portion 330a is provided on the side of the support member 330. The inner circumferential surface of the displacement prevention portion 330a is formed along the shape of the treatment instrument insertion portion 35, and is, for example, substantially U-shaped. The inner circumferential surface abuts on the outer circumferential surface of the treatment instrument insertion portion 35.

[Extension Member 340]

As shown in FIG. 1A, FIG. 1B, FIG. 2A, and FIG. 2B, the extension member 340 is, for example, a bar member. The extension member 340 is integral with the support member 330. The central axis of the extension member 340 is provided parallel to a central axis 31a of the body portion 31 when the advance and retreat assist tool 100 is attached to the endoscope 10.

[Fixing Unit 400]

As shown in FIG. 1A, FIG. 1B, FIG. 4A, and FIG. 4B, the fixing unit 400 fixes the base unit 300 to the endoscope 10 so that the first central axis 311a is provided coaxially with the central axis 35c of the treatment instrument insertion hole portion 35a and the first hole portion 311 faces the treatment instrument insertion hole portion 35a. The fixing unit 400 is provided in the base unit 300.

As shown in FIG. 1A, FIG. 1B, FIG. 2A, and FIG. 2B, the fixing unit 400 has a fixing portion 410 which winds around, for example, the grasping portion 33 and thereby fixes the support member 330 to the grasping portion 33 when the advance and retreat assist tool 100 is attached to the endoscope 10, and a displacement prevention portion 430 which pinches, for example, the body portion 31 and thereby prevents the displacement of the base unit 300 including the extension member 340. The fixing unit 400 may include the above-mentioned base member 320.

[Fixing Portion 410]

As shown in FIG. 1A, FIG. 1B, FIG. 2A, and FIG. 2B, the fixing portion 410 winds around the grasping portion 33 after the displacement prevention portion 330a has abutted on the grasping portion 33. The fixing portion 410 is, for example, a substantially U-shaped belt member. One end portion of the fixing portion 410 is removably fixed to one side surface of the support member 330 by, for example, a screw portion 213c. The other end portion of the fixing portion 410 is removably fixed to the other side surface of the support member 330 by, for example, the screw portion 213c.

[Displacement Prevention Portion 430]

As shown in FIG. 1A, FIG. 1B, FIG. 2A, and FIG. 2B, the displacement prevention portion 430 is fixed to the extension member 340 by, for example, a screw portion 213d to be provided along a direction that intersects at right angles with the direction of the central axis 31a of the body portion 31. The displacement prevention portion 430 is, for example, substantially Y-shaped. An inner circumferential surface of the displacement prevention portion 430 is formed along the shape of the body portion 31, and is provided along the circumference of the central axis 31a of the body portion 31. The inner circumferential surface is, for example, substantially U-shaped, and abuts on the outer circumferential surface of the body portion 31. The displacement prevention portion 430 abuts on the body portion 31 simultaneously with the abutting of the displacement prevention portion 330a on the grasping portion 33.

[First Tubular Member 500]

As shown in FIG. 4A and FIG. 4B, the first tubular member 500 has the third central axis 500a. The first tubular member 500 is provided so that the third central axis 500a is provided along the direction of the second central axis 313a and so that the third central axis 500a is provided coaxially with the second central axis 313a. The first tubular member 500 is formed as a cylindrical member into which the treatment instrument 51 is inserted. The treatment instrument 51 is inserted into the first tubular member 500 from a proximal end portion 500c of the first tubular member 500, and is projected from a distal end portion 500b of the first tubular member 500.

As shown in FIG. 4A, when the first tubular member 500 advances, the treatment instrument 51 is directly inserted into the first hole portion 311. As shown in FIG. 4B, when the first tubular member 500 retreats, the treatment instrument 51 is inserted into the first hole portion 311 via the second hole portion 313. That is, the first tubular member 500 functions as a guide member which guides the treatment instrument 51 to the first hole portion 311.

As shown in FIG. 2B, FIG. 4A, and FIG. 4B, the first tubular member 500 has the above-mentioned third central axis 500a, the distal end portion 500b which is inserted into the second hole portion 313 when the first tubular member 500 advances and which is removed from the second hole portion 313 when the first tubular member 500 retreats, and the proximal end portion 500c to which a proximal end portion 51b of the treatment instrument 51 is fixed by the fixing portion 600. The first tubular member 500 has an opening portion 500d which is provided in a circumferential surface of the first tubular member 500 and with which a later-described protrusion portion 801 is engaged.

As shown in FIG. 4A, the distal end portion 500b is inserted into the second hole portion 313 so that the first tubular member 500 is in communication with the first hole portion 311 when the first tubular member 500 advances. As shown in FIG. 4B, the distal end portion 500b is removed from the second hole portion 313 so that the first tubular member 500 faces the first hole portion 311 when the first tubular member 500 retreats.

As shown in FIG. 4A, the opening portion 500d is provided on the side of the distal end portion 500b so that the opening portion 500d is not inserted into the second hole portion 313 when the distal end portion 500b is inserted into the second hole portion 313. The opening portion 500d is always exposed from the second hole portion 313. The opening portion 500d is, for example, circular. The opening portion 500d functions as a through-hole portion which passes through the first tubular member 500 in a thickness direction of the first tubular member 500. A pair of openings 500d are provided with respect to the third central axis 500a.

[Fixing Portion 600]

As shown in FIG. 2B, FIG. 3A, FIG. 3B, FIG. 4A, and FIG. 4B, the fixing portion 600 is provided at the proximal end portion 500c of the first tubular member 500. The fixing portion 600 fixes the proximal end portion 51b of the treatment instrument 51 to the proximal end portion 500c of the first tubular member 500. The fixing portion 600 has a cylindrical portion 601 through which the treatment instrument 51 is inserted and which is inserted into the proximal end portion 500c of the first tubular member 500, a fixing member 605 which is mounted at the end portion of the cylindrical portion 601 and through which the treatment instrument 51 is inserted, and a fastening portion 603 which functions as a cap to cover the cylindrical portion 601 and the fixing member 605 and which fastens the cylindrical portion 601.

The fastening portion 603 rotates around the axis of the fastening portion 603 and thereby fastens the cylindrical portion 601, and compresses the fixing member 605 by fastening. The fixing member 605 comes into close contact with the proximal end portion 51b of the treatment instrument 51 by compression. As a result, the treatment instrument 51 becomes integral with the first tubular member 500 via the fixing portion 600. The fixing member 605 is formed by, for example, elastic rubber which capable of expansion and contraction.

[Rotary Portion 700]

As shown in FIG. 1A and FIG. 1B, the rotary portion 700 rotates around the third central axis 500a. The rotary portion 700 is formed as a cylindrical member into which the first tubular member 500 is inserted. More specifically, the first tubular member 500 is inserted into the rotary portion 700 so that the central axis of the rotary portion 700 is provided coaxially with the third central axis 500a. As shown in FIG. 4A, the rotary portion 700 has a length such that the proximal end portion 500c of the first tubular member 500 projects outside than the proximal end portion of the rotary portion 700 along the direction of the third central axis 500a when the distal end portion 500b of the first tubular member 500 is inserted in the second hole portion 313 while the first tubular member 500 is inserted in the rotary portion 700. As shown in FIG. 1A and FIG. 1B, when the advance and retreat assist tool 100 is attached to the endoscope 10, the rotary portion 700 is provided adjacent to the grasping portion 33. Thus, the rotary portion 700 functions as an operation knob.

As shown in FIG. 1A and FIG. 1B, the rotary portion 700 has recess portions 701 provided in an outer circumferential surface of the rotary portion 700. The recess portions 701 are provided along the direction of the third central axis 500a. The recess portions 701 are adjacent to each other in a direction around the third central axis 500a. The inner circumferential surface of the recess portion 701 is, for example, smoothly semicircular. As shown in FIG. 5, the recess portions 701 are formed as mounting surfaces to mount the fingers of the left hand grasping the grasping portion 33.

[Configuration of Advance and Retreat Mechanism 800]

The advance and retreat mechanism 800 intervenes between the rotary portion 700 and the first tubular member 500. The advance and retreat mechanism 800 converts the rotation force of the rotary portion 700 to an advance and retreat force of the first tubular member 500, and the advance and retreat mechanism 800 transmits the advance and retreat force to the first tubular member 500 and thereby advances and retreats the first tubular member 500 along the direction of the third central axis 500a, when the rotary portion 700 rotates.

As shown in FIG. 2A, FIG. 2B, FIG. 3A, FIG. 3B, FIG. 4A, and FIG. 4B, the advance and retreat mechanism 800 has the protrusion portion 801, the second tubular member 803, and a third tubular member 805. As shown in FIG. 4A and FIG. 4B, the protrusion portion 801, the second tubular member 803, and the third tubular member 805 intervene between the first tubular member 500 and the rotary portion 700 in the diametrical direction of the first tubular member 500.

[Protrusion Portion 801]

As shown in FIG. 3A, FIG. 3B, FIG. 3C, FIG. 4A, and FIG. 4B, the protrusion portion 801 is provided straight along the diametrical direction of the first tubular member 500 so that the protrusion portion 801 passes through a later-described long opening portion 803d and is inserted into a later-described spiral opening portion 805d. The protrusion portion 801 is engaged with the opening portion 500d, and is thereby engaged with the circumferential surface of the first tubular member 500. As shown in FIG. 3C, the protrusion portion 801 has a diameter such that the protrusion portion 801 abuts on the edge portion of the long opening portion 803d and the edge portion of the spiral opening portion 805d.

[Second Tubular Member 803]

As shown in FIG. 2B, FIG. 3A, FIG. 3B, FIG. 4A, and FIG. 4B, the second tubular member 803 has a fourth central axis 803a, and a distal end portion 803b which is fitted into and thus fixed to the second hole portion 313 so that the fourth central axis 803a is provided along the direction of the second central axis 313a and so that the fourth central axis 803a is provided coaxially with the second central axis 313a. The second tubular member 803 has a proximal end portion 803c fitted into and thus fixed to a fit hole portion 953c of a later-described base member 953, and the long opening portion 803d provided in a circumferential surface of the second tubular member 803 along the direction of the fourth central axis 803a.

As shown in FIG. 4A and FIG. 4B, the distal end portion 803b is formed as a fixed end which is fixed to the base member 310 by, for example, a screw portion 213e when the distal end portion 803b is inserted in the second hole portion 313. The screw portion 213e is inserted through the side surface of the base member 310, and abuts on the circumferential surface of the distal end portion 803b.

As shown in FIG. 4A and FIG. 4B, the proximal end portion 803c is formed as a fixed end which is fixed to the support unit 950 by, for example, a screw portion 213f when the proximal end portion 803c is inserted in the fit hole portion 953c of the support unit 950. The screw portion 213f is inserted through the side surface of the support unit 950, and abuts on the circumferential surface of the proximal end portion 803c.

As a result, the second tubular member 803 is prevented from rotating and moving, and is fixed to the base unit 300 and the support unit 950.

As shown in FIG. 2B, the long opening portion 803d is provided straight from the side of the distal end portion 803b to the side of the proximal end portion 803c. As shown in FIG. 4A and FIG. 4B, the distal end portion of the long opening portion 803d is provided on the side of the distal end portion 803b so that the distal end portion of the long opening portion 803d is not inserted into the second hole portion 313 when the distal end portion 803b is inserted in the second hole portion 313. As shown in FIG. 4A and FIG. 4B, the proximal end portion of the long opening portion 803d is provided on the side of the proximal end portion 803c so that the proximal end portion of the long opening portion 803d is not inserted into the fit hole portion 953c of the later-described support unit 950 when the proximal end portion 803c is inserted in the fit hole portion 953c of the support unit 950. That is, the long opening portion 803d is exposed from the second hole portion 313 and the support unit 950.

As shown in FIG. 4A and FIG. 4B, the long opening portion 803d has a length slightly longer than the length from one edge portion of the later-described spiral opening portion 805d to the other edge portion in the direction of the fourth central axis 803a. One edge portion side of the long opening portion 803d faces one edge portion of the spiral opening portion 805d, and the other edge portion side of the long opening portion 803d faces the other edge portion of the spiral opening portion 805d. The long opening portion 803d is substantially equal in length to the rotary portion 700.

The length of the long opening portion 803d corresponds to the movement amount of the first tubular member 500, and corresponds to the advance and retreat amount of the treatment instrument 51. These are substantially equal in size. The maximum value of the length corresponds to the maximum value of the movement amount and the maximum value of the advance and retreat amount. Each of these maximum values corresponds to the size of the part to be treated with the treatment instrument 51, and has a desired value. The maximum value is, for example, 30 mm.

The long opening portion 803d does not pass through the second tubular member 803 in the direction of the fourth central axis 803a. The long opening portion 803d passes through the first tubular member 500 in the thickness direction of the second tubular member 803. A pair of long openings 803d are provided with respect to the fourth central axis 803a.

Such a second tubular member 803 is formed as a cylindrical member into which the first tubular member 500 is inserted so that part of the long opening portion 803d is in communication with the opening portion 500d and the protrusion portion 801 is inserted through the long opening portion 803d. The second tubular member 803 has a length such that the proximal end portion 500c of the first tubular member 500 projects outside than the proximal end portion 803c of the second tubular member 803 along the direction of the second central axis 313a when the first tubular member 500 is inserted in the second tubular member 803, the distal end portion 500b of the first tubular member 500 is inserted in the second hole portion 313, and the distal end portion 803b of the second tubular member 803 is fitted in the second hole portion 313.

[Third Tubular Member 805]

As shown in FIG. 2B, the third tubular member 805 has a fifth central axis 805a provided coaxially with the third central axis 500a, a distal end portion 805b, a proximal end portion 805c, and the spiral opening portion 805d provided in a circumferential surface of the third tubular member 805 to wind around the fifth central axis 805a.

As shown in FIG. 4A and FIG. 4B, the third tubular member 805 is provided so that the distal end portion 805b is not inserted into the second hole portion 313 and the proximal end portion 805c is not inserted into the support unit 950.

As shown in FIG. 4A and FIG. 4B, the third tubular member 805 is inserted into the rotary portion 700 so that the third tubular member 805 rotates relative to the second tubular member 803 around the fifth central axis 805a together with the rotary portion 700. The third tubular member 805 is fixed to the rotary portion 700 by a screw portion 213g shown in FIG. 2B so that the third tubular member 805 rotates together with the rotary portion 700. Thus, the third tubular member 805 rotates in the same direction as the rotary portion 700. As shown in FIG. 3C, FIG. 4A, and FIG. 4B, the third tubular member 805 functions as a cylindrical member into which the second tubular member 803 is inserted so that part of the spiral opening portion 805d is in communication with part of the long opening portion 803d and so that the protrusion portion 801 inserted through the long opening portion 803d is inserted into the spiral opening portion 805d. Such a third tubular member 805 functions as a cam ring. The third tubular member 805 is substantially equal in length to the long opening portion 803d and the rotary portion 700.

As shown in FIG. 2B, the spiral opening portion 805d is provided from the distal end portion 805b to the proximal end portion 805c in the direction of the fifth central axis 805a. The spiral opening portion 805d does not pass through the third tubular member 805 in the direction of the fifth central axis 805a. The spiral opening portion 805d passes through the third tubular member 805 in the thickness direction of the third tubular member 805. A pair of spiral openings 805d are provided with respect to the third central axis 500a.

[Movement of Advance and Retreat Mechanism 800]

As shown in FIG. 1A, FIG. 1B, FIG. 3A, FIG. 3B, FIG. 3C, FIG. 4A, and FIG. 4B, if the rotary portion 700 rotates around the third central axis 500a, the third tubular member 805 also rotates simultaneously with the rotary portion 700. As a result, the spiral opening portion 805d provided in the third tubular member 805 also rotates.

As shown in FIG. 3A and FIG. 3B, the protrusion portion 801 is in abutment with the edge portion of the spiral opening portion 805d. Thus, in response to the rotation of the spiral opening portion 805d, the protrusion portion 801 is pressed to rotate by the spiral opening portion 805d. As shown in FIG. 3A and FIG. 3B, the protrusion portion 801 is inserted through the long opening portion 803d, and is also in abutment with the edge portion of the long opening portion 803d. Thus, the protrusion portion 801 is pressed to rotate by the spiral opening portion 805d, so that the protrusion portion 801 moves in the long opening portion 803d along the direction of the third central axis 500a.

Thus, the third tubular member 805 rotates in response to the rotation of the rotary portion 700, so that the spiral opening portion 805d rotates. As a result of the rotation of the spiral opening portion 805d, the protrusion portion 801 moves in the long opening portion 803d along the direction of the third central axis 500a by the spiral opening portion 805d.

The protrusion portion 801 abuts on the edge portion of the long opening portion 803d, so that the first tubular member 500 having the distal end portion 500b with which the protrusion portion 801 is engaged is prevented from rotating around the third central axis 500a.

The spiral opening portion 805d rotates, and the protrusion portion 801 moves in the long opening portion 803d along the direction of the third central axis 500a, so that the first tubular member 500 having the distal end portion 500b with which the protrusion portion 801 is engaged advances and retreats along the direction of the third central axis 500a while the rotation of the first tubular member 500 around the third central axis 500a is prevented. As a result, the treatment instrument 51 fixed to the first tubular member 500 advances and retreats.

The distal end portion 803b of the second tubular member 803 is fitted into and thus fixed to the second hole portion 313, and the proximal end portion 803c of the second tubular member 803 is fitted into and thus fixed to the fit hole portion 953c of the support unit 950. Therefore, the second tubular member 803 remains fixed. This prevents the long opening portion 803d from rotating in the same manner as the spiral opening portion 805d.

The protrusion portion 801 only moves in the long opening portion 803d along the direction of the third central axis 500a. Therefore, the first tubular member 500 only advances and retreats along the direction of the third central axis 500a, and the rotation of the first tubular member 500 around the third central axis 500a is prevented. Similarly, the treatment instrument 51 only advances and retreats, and the rotation of the treatment instrument 51 around the third central axis 500a is prevented.

Thus, the advance and retreat mechanism 800 advances and retreats the treatment instrument 51 while the treatment instrument 51 is prevented from rotating around the third central axis 500a in response to the rotation of the rotary portion 700 around the third central axis 500a when the rotary portion 700 rotates around the third central axis 500a.

[Regulating Mechanism 900]

The regulating mechanism 900 regulates the advance and retreat of the first tubular member 500 when the first tubular member 500 advances and retreats along the direction of the third central axis 500a so that the distal end portion 500b of the first tubular member 500 moves along the direction of the third central axis 500a between a part where the first hole portion 311 provided on the distal end portion side of the rotary portion 700 is in communication with the second hole portion 313 and a position on the side where the first tubular member 500 provided on the proximal end portion side of the rotary portion 700 comes off the rotary portion 700.

The regulating mechanism 900 is formed by the protrusion portion 801 and the edge portion of the spiral opening portion 805d.

[Support Unit 950]

As shown in FIG. 1A, FIG. 1B, FIG. 2A, FIG. 2B, FIG. 3A, FIG. 3B, FIG. 4A, and FIG. 4B, the support unit 950 supports the first tubular member 500 via the protrusion portion 801, the second tubular member 803, and the third tubular member 805 so that the third central axis 500a is provided coaxially with the second central axis 313a, the first tubular member 500 moves along the direction of the third central axis 500a, and thus the first tubular member 500 is prevented from moving in a direction that intersects at right angles with the direction of the third central axis 500a.

The support unit 950 has a base member 951 which is provided along the direction of the third central axis 500a and which is provided on the side of the rotary portion 700, and a base member 953 which is provided along the direction that intersects at right angles with the direction of the third central axis 500a and which is provided above the rotary portion 700.

The base member 951 has one end portion fixed to the base member 310 by, for example, a screw portion 213h, and the other end portion fixed to the base member 953 by, for example, a screw portion 213i.

The base member 953 has the fit hole portion 953c into which the proximal end portion 803c of the second tubular member 803 is fitted. The base member 953 is fixed by, for example, the screw portion 213f to the proximal end portion 803c of the second tubular member 803 which is fitted into the fit hole portion 953c.

The support unit 950 supports the first tubular member 500 via the base member 310 and the second tubular member 803. The support unit 950 supports the third tubular member 805 via the base member 310, the second tubular member 803, and a washer 955.

[Function]

[Attachment of Advance and retreat assist tool 100 to Endoscope 10]

As shown in FIG. 1A, FIG. 1B, FIG. 4A, and FIG. 4B, the fixing unit 400 fixes the base unit 300 to the endoscope 10 so that the first hole portion 311 faces the treatment instrument insertion hole portion 35a.

At the same time, the displacement prevention portion 330a pinches the treatment instrument insertion portion 35 and thereby prevents the displacement of the base unit 300 including the support member 330. The displacement prevention portion 330a also prevents the displacement of the base unit 300 so that the base member 320 surrounds the forceps plug 36, the first hole portion 311 faces the treatment instrument insertion hole portion 35a, and the first central axis 311a of the first hole portion 311 is provided coaxially with the central axis 35c of the treatment instrument insertion hole portion 35a. The fixing portion 410 winds around the grasping portion 33, and fixes the support member 330 to the grasping portion 33. The displacement prevention portion 430 pinches the body portion 31 and thereby prevents the displacement of the base unit 300 including the extension member 340.

As shown in FIG. 10, the direction of the third central axis 500a is the same as the direction of the second central axis 313a, and the angle θ1>the angle θ2. Therefore, as shown in FIG. 1A and FIG. 1B, when the advance and retreat assist tool 100 is attached to the endoscope 10, the rotary portion 700 is slanted toward the central axis 33a of the grasping portion 33 relative to the central axis 35c of the treatment instrument insertion hole portion 35a. The rotary portion 700 is provided adjacent to the grasping portion 33.

[Provide of Treatment Instrument 51]

After the insertion portion 20 of the endoscope 10 is inserted in the body cavity, the treatment instrument 51 is inserted from the fixing portion 600, and then inserted through the first tubular member 500. The treatment instrument 51 is further inserted into the endoscope 10 from the treatment instrument insertion portion 35. The distal end portion 51a of the treatment instrument 51 projects from the distal opening portion 35b. The length of the projecting distal end portion 51a of the treatment instrument 51 is a desired length.

The fastening portion 603 rotates around the axis of the fastening portion 603 and thereby fastens the cylindrical portion 601, and compresses the fixing member 605 by fastening. The fixing member 605 comes into close contact with the proximal end portion 51b of the treatment instrument 51 by compression. As a result, the treatment instrument 51 is fixed to the advance and retreat assist tool 100 via the fixing portion 600 and the first tubular member 500.

When the treatment instrument 51 is removed from the endoscope 10, this movement is performed in the opposite procedure.

[Grasp of Endoscope 10 and Treatment Instrument 51]

As shown in FIG. 5, the grasping portion 33 is grasped by the surgeon with the left hand, the rotary portion 700 adjacent to the grasping portion 33 is operated by, for example, the little finger or third finger of the left hand, and the bending operation portion is operated by the thumb of the left hand.

[Advance Operation of Treatment Instrument 51]

When the rotary portion 700 is operated by, for example, the little finger or third finger of the left hand, the rotary portion 700 rotates in one direction around the third central axis 500a. The third tubular member 805 also rotates simultaneously with the rotary portion 700. As a result, the spiral opening portion 805d provided in the third tubular member 805 also rotates.

As a result of the rotation of the spiral opening portion 805d, the protrusion portion 801 moves in the long opening portion 803d along the direction of the third central axis 500a by the spiral opening portion 805d.

The first tubular member 500 having the distal end portion 500b with which the protrusion portion 801 is engaged advances along the direction of the third central axis 500a. As a result, the treatment instrument 51 fixed to the first tubular member 500 advances.

Since the second tubular member 803 is fixed, the long opening portion 803d is fixed, so that the long opening portion 803d is prevented from rotating in the same manner as the spiral opening portion 805d. Therefore, the protrusion portion 801 only moves in the long opening portion 803d along the direction of the third central axis 500a. Thereby, the first tubular member 500 only advances along the direction of the third central axis 500a, and the rotation of the first tubular member 500 around the third central axis 500a is prevented. Similarly, the treatment instrument 51 only advances, and the rotation of the treatment instrument 51 around the third central axis 500a is prevented.

The protrusion portion 801 abuts on one edge portion of the spiral opening portion 805d, so that the advance of the first tubular member 500 is stopped, and the advance of the treatment instrument 51 is stopped.

[Retreat Operation of Treatment Instrument 51]

When the rotary portion 700 is operated by, for example, the little finger or third finger of the left hand, the rotary portion 700 rotates in the other direction around the third central axis 500a. The third tubular member 805 also rotates simultaneously with the rotary portion 700. As a result, the spiral opening portion 805d provided in the third tubular member 805 also rotates.

As a result of the rotation of the spiral opening portion 805d, the protrusion portion 801 moves in the long opening portion 803d along the direction of the third central axis 500a by the spiral opening portion 805d.

The first tubular member 500 having the distal end portion 500b with which the protrusion portion 801 is engaged retreats along the direction of the third central axis 500a. As a result, the treatment instrument 51 fixed to the first tubular member 500 retreats.

Since the second tubular member 803 is fixed, the long opening portion 803d is fixed, so that the long opening portion 803d is prevented from rotating in the same manner as the spiral opening portion 805d. Therefore, the protrusion portion 801 only moves in the long opening portion 803d along the direction of the third central axis 500a. Thereby, the first tubular member 500 only retreats along the direction of the third central axis 500a, and the rotation of the first tubular member 500 around the third central axis 500a is prevented. Similarly, the treatment instrument 51 only retreats, and the rotation of the treatment instrument 51 around the third central axis 500a is prevented.

The protrusion portion 801 abuts on the other edge portion of the spiral opening portion 805d, so that the advance of the first tubular member 500 is stopped, and the advance of the treatment instrument 51 is stopped. This also prevents the first tubular member 500 from coming off the rotary portion 700.

[Effect]

Thus, according to the present embodiment, the second central axis 313a (the third central axis 500a) is slanted relative to the first central axis 311a, and the rotary portion 700 rotates around the third central axis 500a. The advance and retreat mechanism 800 converts the rotation force of the rotary portion 700 to an advance and retreat force, and advances and retreats the first tubular member by the advance and retreat force. Thus, according to the present embodiment, it is possible to prevent the size increase of the endoscope 10, ensure that the treatment instrument 51 is finely advanced and retreated by one hand grasping the grasping portion 33, and prevent a burden on the surgeon.

More specifically, according to the present embodiment, in the advance and retreat mechanism 800, the rotation force of the rotary portion 700 is not transmitted directly to the first tubular member 500, converted to an advance and retreat force by the second tubular member 803 and the third tubular member 805, and transmitted indirectly to the first tubular member 500. Thus, according to the present embodiment, it is possible to prevent the treatment instrument 51 from rapidly advancing and retreating, and finely advance and retreat the treatment instrument 51.

According to the present embodiment, the treatment instrument 51 can be advanced and retreated by the advance and retreat mechanism 800 without rotating together with the rotary portion 700.

According to the present embodiment, the angle θ1>the angle θ2, so that the rotary portion 700 can be provided adjacent to the grasping portion 33. According to the present embodiment, this ensures that the fingers of one hand grasping the grasping portion 33 can reach the rotary portion 700 and that the treatment instrument 51 can be advanced and retreated while the grasping portion 33 is grasped. According to the present embodiment, the surgeon can handle the grasping of the endoscope 10 and the advance and retreat of the first tubular member 500 with one hand. According to the present embodiment, the size increase of the endoscope 10 can be prevented.

According to the present embodiment, the bending operation portion 37 and the switch portion 39 are provided in the grasping portion 33. Thus, according to the present embodiment, the surgeon can handle the grasping of the endoscope 10 and the advance and retreat of the first tubular member 500 with one hand, and also operate the bending operation portion 37 and the switch portion 39.

According to the present embodiment, the protrusion portion 801 abuts on the edge portion of the spiral opening portion 805d, so that the advance and retreat of the first tubular member 500 can be regulated, and the advance and retreat of the treatment instrument 51 can be regulated.

The long opening portion 803d may have a length slightly shorter than the length from one edge portion of the spiral opening portion 805d to the other edge portion in the direction of the fourth central axis 803a. In this case, the protrusion portion 801 abuts on the edge portion of the long opening portion 803d, so that the advance and retreat of the first tubular member 500 can be regulated, and the advance and retreat of the treatment instrument 51 can be regulated. The regulating mechanism 900 is then formed by the protrusion portion 801 and the edge portion of the long opening portion 803d.

The long opening portion 803d may have a length substantially equal to the length from one edge portion of the spiral opening portion 805d to the other edge portion in the direction of the fourth central axis 803a. In this case, one edge portion of the long opening portion 803d faces one edge portion of the spiral opening portion 805d, and the other edge portion of the long opening portion 803d faces the other edge portion of the spiral opening portion 805d. In this case, the protrusion portion 801 abuts on the edge portion of the long opening portion 803d and the edge portion of the spiral opening portion 805d, so that the advance and retreat of the first tubular member 500 can be regulated, and the advance and retreat of the treatment instrument 51 can be regulated. The regulating mechanism 900 is then formed by the protrusion portion 801, the edge portion of the long opening portion 803d, and the end portion of the spiral opening portion 805d.

Thus, the regulating mechanism 900 has only to be formed by the protrusion portion 801 and at least one of the end portion of the spiral opening portion 805d and the edge portion of the long opening portion 803d.

According to the present embodiment, the support unit 950 can prevent the first tubular member 500 from moving in a direction that intersects at right angles with the direction of the third central axis 500a. Thus, according to the present embodiment, the first tubular member 500 and the treatment instrument 51 can be advanced and retreated.

According to the present embodiment, it is possible to freely adjust the advance and retreat amount of the treatment instrument 51 by setting the length of the long opening portion 803d and the length of the spiral opening portion 805d to desired lengths.

According to the present embodiment, for example, the first tubular member 500 may have an unshown index which is provided on the outer circumferential surface of the first tubular member 500 and which indicates the advance and retreat position of the treatment instrument 51. When the first tubular member 500 is exposed from the rotary portion 700 in accordance with the advance and retreat, the index portion is exposed from the rotary portion 700. Thus, the surgeon can recognize the advance and retreat position of the treatment instrument 51 by checking the index portion.

[First Modification]
[Configuration]

In the first embodiment described above, the advance and retreat mechanism 800 has the protrusion portion 801, the second tubular member 803, and a third tubular member 805. However, the advance and retreat mechanism 800 does not need to be limited to this. As shown in FIG. 6, FIG. 7A, and FIG. 7B, the advance and retreat mechanism 800 may have the protrusion portion 801, the first tubular member 500, and the second tubular member 803.

The first tubular member 500 has a spiral opening portion 500e which is provided in the circumferential surface of the first tubular member 500 to wind around the third central axis 500a. The spiral opening portion 500e is provided from the side of the distal end portion 500b to the side of the proximal end portion 500c in the direction of the third central axis 500a. A pair of spiral openings 500e are provided with respect to the third central axis 500a.

The second tubular member 803 is inserted in the rotary portion 700 so that the second tubular member 803 rotates around the third central axis 500a together with the rotary portion 700 when the rotary portion 700 rotates around the third central axis 500a. The distal end portion 803b of the second tubular member 803 is inserted in the second hole portion 313 so that the second tubular member 803 rotates around the third central axis 500a, and the proximal end portion 803c of the second tubular member 803 is inserted in a hole portion 953e of the base member 953. The second tubular member 803 is supported by the base member 310 and the base member 953 so that the second tubular member 803 is rotatable and the detachment the second tubular member 803 is prevented.

The second tubular member 803 has the protrusion portion 801 which is provided on the inner circumferential surface of the second tubular member 803 and which is inserted into the spiral opening portion 500e. Thus, the second tubular member 803 has a through-hole portion 803f which is provided along the direction that intersects at right angles with the third central axis 500a and which passes through the second tubular member 803. The through-hole portion 803f is provided on the side of the proximal end portion 803c of the second tubular member 803. The protrusion portion 801 is provided in the through-hole portion 803f so that the protrusion portion 801 passes through the through-hole portion 803f and is then inserted into the spiral opening portion 500e.

The protrusion portion 801 passes through the rotary portion 700 and is then inserted into the through-hole portion 803f. Thus, the protrusion portion 801 fixes the rotary portion 700 to the second tubular member 803 so that the second tubular member 803 rotates together with the rotary portion 700.

[Movement of Advance and Retreat Mechanism 800]

If the rotary portion 700 rotates around the third central axis 500a, the second tubular member 803 also rotates simultaneously with the rotary portion 700. As a result, the protrusion portion 801 provided in the through-hole portion 803f of the second tubular member 803 also rotates.

The protrusion portion 801 is in abutment with the edge portion of the spiral opening portion 500e. Thus, in response to the rotation of the protrusion portion 801, the spiral opening portion 500e is pressed to rotate by the protrusion portion 801. The second tubular member 803 including the protrusion portion 801 are supported by the base member 310 and the base member 953 and is therefore only rotate, and the movement of the second tubular member 803 along the direction of the third central axis 500a is prevented. The rotary portion 700 in which the second tubular member 803 is inserted also only rotates, and the movement of the rotary portion 700 is prevented.

Thus, the spiral opening portion 500e is pressed to rotate by the protrusion portion 801, so that the first tubular member 500 including the spiral opening portion 500e advances and retreats along the direction of the third central axis 500a. The protrusion portion 801 abuts on the edge portion of the long opening portion 803d, so that the rotation of the first tubular member 500 around the third central axis 500a is prevented.

Thus, the second tubular member 803 rotates in response to the rotation of the rotary portion 700, and the protrusion portion 801 rotates in the same manner as the rotary portion 700. The first tubular member 500 having the spiral opening portion 500e with which the protrusion portion 801 is engaged advances and retreats along the direction of the third central axis 500a by the rotation of the protrusion portion 801 while the rotation of the first tubular member 500 around the third central axis is prevented.

[Effect]

In the present modification, the third tubular member 805 can be omitted, and the configuration of the advance and retreat assist tool 100 can be simplified. In the present modification, the second tubular member 803 and the rotary portion 700 are separate from each other, but are not limited to this. The second tubular member 803 and the rotary portion 700 may be integral. Thus, in the present modification, the configuration of the advance and retreat assist tool 100 can be more simplified.

[Second Modification]

As shown in FIG. 8A and FIG. 8B, the regulating mechanism 900 has a regulating member 901 which is provided in the base member 953 and which regulates the advance and retreat of the first tubular member 500. The regulating member 901 has a long opening portion 901a. The long opening portion 901a is provided along the direction of the second central axis 313a. The long opening portion 901a passes through the regulating member 901 in the thickness direction of the regulating member 901. The long opening portion 901a is shorter than, for example, the long opening portion 803d. A screw portion 213j fixed to the side surface of the proximal end portion 500c of the first tubular member 500 passes through the long opening portion 901a.

The rotation of the treatment instrument 51 is prevented by the movement of the screw portion 213j along the long opening portion 901a. The advance and retreat of the treatment instrument 51 are regulated by the abutting of the screw portion 213j on the edge portion of the long opening portion 901a.

[Effect]

In the present modification, the advance and retreat of the first tubular member 500 can be regulated, and the advance and retreat of the treatment instrument 51 can be regulated within a range shorter than the length of the long opening portion 803d.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An advance and retreat assist tool of an endoscopic treatment instrument, the advance and retreat assist tool comprising:
   a base unit provided in an endoscope including a treatment instrument insertion hole portion into which the endoscopic treatment instrument is inserted and including a hole portion which is in communication with the treatment instrument insertion hole portion;
   a rotary portion, which rotates relative to the base unit around a central axis extending along a central axis of the hole portion, is formed as a cylindrical member, and is configured to be manually manipulated while in use;
   an advance and retreat mechanism provided inside the rotary portion, which converts a rotation force of the rotary portion to an advance and retreat force in the central axis direction of the rotary portion when the rotary portion rotates;
   a first tubular member inserted in the rotary portion being provided in the advance and retreat mechanism, the first tubular member being advanced and retreated in the central axis direction of the rotary portion by the advance and retreat force transmitted from the advance and retreat mechanism when the rotary portion rotates, the endoscopic treatment instrument is inserted into the first tubular member so that the endoscopic treatment instrument is inserted into the treatment instrument insertion hole portion; and
   a fixing portion which fixes the endoscopic treatment instrument to the first tubular member so that the endoscopic treatment instrument can be advanced and retreated together with the first tubular member.

2. The advance and retreat assist tool of the endoscopic treatment instrument according to claim 1, wherein the first tubular member is provided in the rotary portion so that an axis of the first tubular member is along a rotation axis of the rotary portion.

3. The advance and retreat assist tool of the endoscopic treatment instrument according to claim 1, wherein the hole portion of the base unit includes a first hole portion having a first central axis provided along a central axis of the treatment instrument insertion hole portion, and being in communication with the treatment instrument insertion hole portion, and a second hole portion which has a second central axis slanted relative to the first central axis and which is in communication with the first hole portion.

4. The advance and retreat assist tool of the endoscopic treatment instrument according to claim 3, wherein the first tubular member has a third central axis provided coaxially with the second central axis, and the first tubular member advances and retreats along the direction of the third central axis in response to the rotation of the rotary portion.

5. The advance and retreat assist tool of the endoscopic treatment instrument according to claim 3, wherein the central axis direction of the treatment instrument insertion hole portion is slanted relative to the central axis direction of the grasping portion of the endoscope, and an angle .theta.1>an angle .theta.2 in which an angle formed between the central axis direction of the treatment instrument insertion hole portion and the central axis direction of the grasping portion is the angle .theta.1, and an angle formed between the direction of the second central axis and the central axis direction of the grasping portion is the angle .theta.2.

6. The advance and retreat assist tool of the endoscopic treatment instrument according to claim 1, the advance and retreat assist tool being removably attached to the endoscope, and further including a fixing unit which removably fixes the base unit to the endoscope and removably attached to the base unit.

7. The advance and retreat assist tool of the endoscopic treatment instrument according to claim 6, wherein the hole portion of the base unit includes a first hole portion through which the endoscopic treatment instrument is inserted, and the fixing unit fixes the base unit to the endoscope so that the first hole portion faces the treatment instrument insertion hole portion.

8. The advance and retreat assist tool of the endoscopic treatment instrument according to claim 7, wherein the fixing unit fixes the base unit to the endoscope so that the first central axis of the first hole portion is provided coaxially with the central axis of the treatment instrument insertion hole portion.

9. The advance and retreat assist tool of the endoscopic treatment instrument according to claim 1, wherein the advance and retreat mechanism includes a protrusion portion provided along the diametrical direction of the first tubular member, a second tubular member which includes a long opening portion provided in a circumferential surface of the second tubular member along a longitudinal axis direction, the first tubular member being inserted in the second tubular member so that the protrusion portion is inserted through the long opening portion, and a third tubular member including a spiral opening portion in circumferentially which is partly in communication with the long opening portion and into which the protrusion portion is inserted, the second tubular member being inserted into the third tubular member so that the protrusion portion inserted through the long opening portion is inserted into the spiral opening portion, the third tubular member being inserted into the rotary portion so that the third tubular member rotates together with the rotary portion.

10. The advance and retreat assist tool of the endoscopic treatment instrument according to claim 1, wherein the advance and retreat mechanism includes a spiral opening portion provided in the circumferential surface of the first tubular member, and a second tubular member including, on its inner circumferential surface, a protrusion portion which is inserted into the spiral opening portion, the first tubular member being inserted in the second tubular member so that the protrusion portion is engaged with the spiral opening portion, the second tubular member being inserted into the rotary portion so that the second tubular member rotates together with the rotary portion.

11. The advance and retreat assist tool of the endoscopic treatment instrument according to claim 1, wherein the fixing portion is provided in the first tubular member and fixes the proximal end portion of the endoscopic treatment instrument to the proximal end portion of the first tubular member.

12. The advance and retreat assist tool of the endoscopic treatment instrument according to claim 1, further comprising a regulating mechanism which regulates the advance and retreat of the first tubular member when the first tubular member advances and retreats.

13. The advance and retreat assist tool of the endoscopic treatment instrument according to claim 1, wherein the proximal end portion of the first tubular member projects outside than the proximal end portion of the rotary portion.

14. The advance and retreat assist tool of the endoscopic treatment instrument according to claim 1, further comprising a support unit which supports the first tubular member so that the first tubular member is prevented from moving in a direction that intersects at right angles with the direction of the advance and retreat of the first tubular member.

15. An endoscopic system comprising: an endoscope including a treatment instrument insertion hole portion; the advance and retreat assist tool of the endoscopic treatment instrument according to claim 1 provided in the endoscope; and the endoscopic treatment instrument which is inserted into the endoscope from the treatment instrument insertion hole portion and which is assisted by the advance and retreat assist tool in advancing and retreating.

16. The advance and retreat assist tool of the endoscopic treatment instrument according to claim 1, wherein the rotary portion rotates relative to the base unit along a central axis identical to the central axis of the hole portion.

* * * * *